United States Patent [19]

Fryberg et al.

[11] 4,407,935
[45] Oct. 4, 1983

[54] PHOTOGRAPHIC RECORDING MATERIAL

[75] Inventors: Mario Fryberg, Praroman-le-Mouret; David G. Leppard, Rheinfelden, both of Switzerland

[73] Assignee: Ciba-Geigy AG, Basel, Switzerland

[21] Appl. No.: 339,816

[22] Filed: Jan. 15, 1982

[30] Foreign Application Priority Data

Jan. 20, 1981 [CH] Switzerland .......................... 352/81

[51] Int. Cl.³ .......................... G03C 5/30; G03C 1/06
[52] U.S. Cl. .................................... 430/487; 430/564; 430/600; 430/601; 430/446; 430/448
[58] Field of Search ............... 430/487, 564, 600, 601, 430/446, 448

[56] References Cited

U.S. PATENT DOCUMENTS 3,385,708  5/1968  Grabhöfer et al. ............... 430/487
4,185,006  1/1980  Rasberger et al. ............... 524/100

FOREIGN PATENT DOCUMENTS 1430998  4/1976  United Kingdom ............... 430/487

Primary Examiner—Won H. Louie, Jr.
Attorney, Agent, or Firm—Joseph G. Kolodny

[57] ABSTRACT

The compounds of the formula

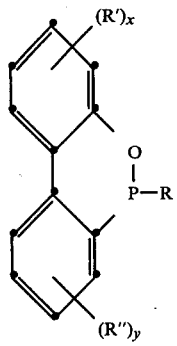

in which R is amino, cyclic amino, aryloxy or a group of the formula

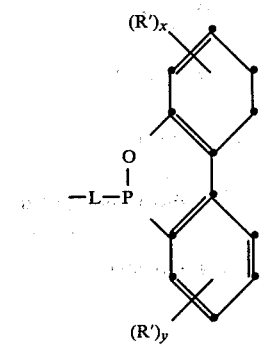

in which L is a radical of the formula =N-Z, with Z being alkyl or cycloalkyl, or is a heterocyclic radical, aryleneoxy or oxyaryleneoxy and R' and R" are hydrogen, alkyl or halogen, and x and y are 0, 1, 2 or 3, are suitable development accelerators for the development of exposed photographic materials containing silver halide. They accelerate the reduction of the exposed silver salt to silver and thus enhance the sensitivity of the photographic material.

22 Claims, No Drawings

PHOTOGRAPHIC RECORDING MATERIAL

The present invention relates to photographic recording material which contains at least one development accelerator in at least one silver halide emulsion layer or in a colloid layer adjacent to the silver halide emulsion layer.

It is known that the sensitivity of photographic silver halide emulsions can be increased indirectly or directly by an addition of development accelerators or chemical sensitisers. Compounds of this type have been described, for example, in British patent specification No. 1,430,998 and in German Offenlegungsschrift No. 2,627,878. In many cases, however, these compounds have only a very weak sensitivity-enhancing activity. They also tend to cause fogging and frequently have a very low chemical and thermal stability.

It is thus the object of the present invention to make new photographic recording materials available, in which development accelerators are used which have a high senstitivity-enhancing activity, without at the same time showing the disadvantages mentioned.

Derivatives of oxaphosphorine for use in layers of photographic materials have now been found, which derivatives impart the desired properties to the recording material.

The present invention therefore relates to a photographic recording material which contains at least one development accelerator in at least one silver halide emulsion layer or in a colloid layer adjacent to the silver halide emulsion layer, wherein the development accelerator is of the formula $$A-R \qquad (1)$$

in which A is a dibenzo[c,e][1,2]oxaphosphorine radical of the formula

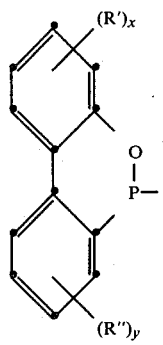

(2)

in which R' and R" independently of one another are hydrogen, substituted or unsubstituted alkyl having 1 to 4 carbon atoms or halogen, x and y independently of one another are 0, 1, 2 or 3 and R is substituted or unsubstituted amino, substituted or unsubstituted cyclic amino, substituted or unsubstituted aryloxy or a group of the formula

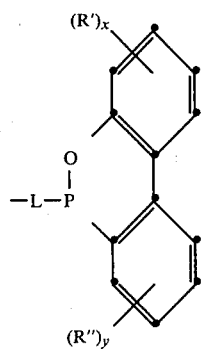

(3)

in which L is a radical of the formula =N—Z, with Z being substituted or unsubstituted alkyl or cycloalkyl, or a substituted or unsubstituted 5-membered or 6-membered, saturated or unsaturated ring which contains at least 2 heteroatoms and which is bonded to the oxaphosphorine radicals via the hetero-atoms, or substituted or unsubstituted aryleneoxy, substituted or unsubstituted oxyaryleneoxy or a radical of the formula —$NB_1$—E—$NB_2$—, in which $B_1$ and $B_2$ independently of one another are hydrogen, alkyl or the radical A and E is alkylene or

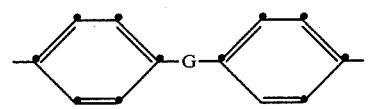

in which G is —O—, —S— or alkylene, and R', R", x and y are as defined above.

The invention also relates to the use of the photographic recording material for the production of photographic images.

Furthermore, the invention relates to the photographic images produced with the photographic recording material.

The invention also relates to a process for the preparation of the photographic recording material.

Moreover, the invention relates to a developing bath containing a development accelerator of formula (1) and being suitable for developing exposed photographic materials.

The substituent A in compounds of the formula (1) is a dibenzo[c,e][1,2]oxaphosphorine radical, in which the two aromatic systems can be substituted or unsubstituted. Possible substituents are R' and R". Independently of one another, these are hydrogen or substituted or unsubstituted alkyl having 1 to 4 carbon atoms. Examples of substituents of these alkyl radicals are halogen, such as chlorine and bromine, and also methoxy, ethoxy, cyano or nitro. Chlorine, methoxy and cyano are preferred. Methyl and ethyl are particularly suitable alkyl radicals. If R' and R" independently of one another are halogen, chlorine and bromine are preferred.

The indices x and y independently of one another are 0, 1, 2 or 3, preferably 0 or 1.

R is substituted amino of the formula —$NR^1R^2$. In this, $R^1$ and $R^2$ independently of one another are hydrogen or alkyl having 1 to 22 carbon atoms, it being possible for the alkyl radicals to be straight-chain or branched, for example methyl, ethyl, propyl, i-propyl, butyl, i-butyl, tert-butyl, amyl, tert-amyl (1,1-dimethylpropyl), 1,1,3,3-tetramethylbutyl, 1-methylethylpentyl, hexyl, 1-methylpentyl, neopentyl, 1-, 2- or 3-methylhexyl, heptyl, n-octyl, tert-octyl, 2-ethylhexyl, n-nonyl, isononyl, tert-nonyl, decyl, tert-decyl, undecyl and also dodecyl, tetradecyl, hexadecyl, octadecyl, nonadecyl or eicosyl as well as the respective isomers.

Alkyl radicals having 1 to 18, in particular 1 to 12, carbon atoms are preferred. Alkyl radicals having 1 to 8 carbon atoms are very particularly suitable. The alkyl radicals can be substituted by halogen, for example fluorine, chlorine or bromine, or by alkoxy having 1 to 4 carbon atoms or phenyl.

$R^1$ and $R^2$ can also be alkenyl having 2 to 12 carbon atoms. With respect to their chemical structure, they are derived from the abovementioned alkyl radicals, 1, 2 or 3 double bonds, preferably 1 double bond, being present in the alkenyl radical. Possible substituents of the alkenyl radicals are halogen, for example bromine or chlorine, or alkoxy, for example methoxy or ethoxy.

Alkenyl radicals having 2 to 6, in particular 3, carbon atoms are preferred.

Moreover, $R^1$ and $R^2$ independently of one another can be alkynyl having 2 to 18 carbon atoms. These can be the alkynyl radicals corresponding to the alkyl radicals mentioned, 1, 2 or 3 triple bonds, preferably 1 triple bond being present in the alkynyl radical. Suitable substituents of the alkynyl radicals can be halogen, for example fluorine, chlorine or bromine, and also cyano, nitro or methoxy. Alkynyl radicals having 2 to 6, in particular 3, carbon atoms are preferred.

$R^1$ and $R^2$ independently of one another can also be substituted or unsubstituted cycloalkyl having 6 to 8, preferably 6, carbon atoms. Preferred substituents can be methyl and tert-butyl.

Substituted or unsubstituted aryl $R^1$ and $R^2$, independently of one another, are phenyl or naphthyl. These radicals can be substituted by alkyl having 1 to 6 carbon atoms, for example methyl, ethyl, propyl, i-propyl, butyl, i-butyl, tert-butyl, amyl, tert-amyl, hexyl, 1,1,3,3-tetramethylbutyl, 1-methylpentyl or neopentyl. The aryl systems can be substituted by up to 3 such alkyl radicals. The preferred aryl is phenyl. Methyl, tert-butyl, tert-amyl and hexyl are preferred aryl substituents.

If $R^1$ and $R^2$ independently of one another are a substituted or unsubstituted, saturated or unsaturated heterocyclic radical containing at least one nitrogen atom and having 4 or 5 carbon atoms, saturated systems, preferably systems having 5 carbon atoms, are particularly suitable. Possible substituents of these systems are alkyl radicals having 1 to 4 carbon atoms, and up to 6 such alkyl radicals can be bonded to a heterocyclic ring. The preferred alkyl radicals are methyl and tert-butyl.

R can also be substituted or unsubstituted cyclic amino. In that case, the radicals $R^1$ and $R^2$ in the formula

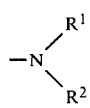

conjointly form an alkylene chain having 4 or 5, preferably 5, carbon atoms or they form divalent radicals of the formula —CH$_2$CH$_2$—O—CH$_2$CH$_2$— or —CH$_2$CH$_2$—NT—CH$_2$CH$_2$—, in which T is hydrogen or alkyl having 1 to 4 carbon atoms, in particular methyl.

If R is substituted or unsubstituted aryloxy, such as phenoxy or naphthoxy, the phenoxy radical is preferred. The latter can, like the naphthoxy radical, be substituted by 1 to 4 substituents and it can be, for example, of the formula

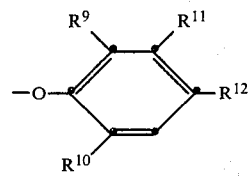

In this formula, $R^9$ and $R^{10}$ independently of one another are hydrogen or alkyl having 1 to 12 carbon atoms. Examples of the alkyl radicals are given in the definitions of $R^1$ and $R^2$. These radicals can be further substituted by phenyl, and the phenyl radical or radicals can carry methyl groups or tert-butyl groups as further substituents. Methyl, tert-butyl, tert-amyl and tert-octyl are preferred alkyl radicals.

$R^{11}$ is hydrogen or substituted or unsubstituted alkyl having 1 to 4 carbon atoms. Methyl, i-propyl, butyl and tert-butyl are preferred alkyl groups. Possible substituents of these alkyl radicals are methoxy, cyano or nitro.

$R^{12}$ is hydrogen or substituted or unsubstituted alkyl having 1 to 12 carbon atoms. The corresponding alkyl radicals mentioned above are possible examples. These can be further substituted by alkoxy having 1 to 18 carbon atoms. Octadecyloxy, hexadecyloxy, tert-octyloxy, tert-nonyloxy, tert-amyloxy, tert-butoxy, ethoxy and methoxy are preferred alkoxy radicals. Further examples of suitable alkoxy radicals can be derived from the above listing of alkyl radicals in the definitions of $R^1$ and $R^2$. The alkyl radicals can also be substituted by carbalkoxy having 2 to 24, in particular 2 to 18, carbon atoms.

If $R^{12}$ is substituted or unsubstituted alkoxy having 1 to 18 carbon atoms, alkoxy radicals having not more than 12 carbon atoms are preferred. Possible examples are the alkoxy radicals mentioned above. Alkoxy radicals having 1 to 4 carbon atoms, for example methoxy, ethoxy, propoxy, butoxy or tert-butoxy, are also particularly suitable. The alkoxy radicals can be further substituted by carbalkoxy having 2 to 4 carbon atoms.

$R^{12}$ can also be carbalkoxy having 2 to 24, in particular 2 to 19, carbon atoms. The corresponding alkoxy radicals having 1 to 18 carbon atoms can be derived from the above listing of alkyl radicals in the definitions of $R^1$ and $R^2$. The alkoxy radicals can be further substituted by methoxy, halogen, for example chlorine or bromine, and also by cyano or nitro.

Furthermore, $R^{12}$ can be thioalkyl having 1 to 18 carbon atoms. With respect to its chemical structure, this is derived from the abovementioned alkoxy radicals. In particularly suitable thioalkyl compounds, the alkyl radical is a methyl, ethyl, butyl, tert-butyl, pentyl or hexyl group. The alkyl radical can be unsubstituted or substituted by methoxy, ethoxy, halogen, for example chlorine or bromine, or carbalkoxy having 2 to 4 carbon atoms.

$R^{12}$ can also be a group of the formula —CO—NR$^{13}$R$^{14}$, in which $R^{13}$ and $R^{14}$ independently of one another are hydrogen or substituted or unsubstituted alkyl having 1 to 4 carbon atoms, for example methyl, ethyl, propyl, butyl and tert-butyl. These groups can be further substituted by alkoxy, for example methoxy or ethoxy, or by carbalkoxy having 2 to 4 carbon atoms.

$R^{13}$ and $R^{14}$ independently of one another can also be alkenyl having 3 to 6, in particular 3, carbon atoms.

Moreover, $R^{11}$ and $R^{12}$ can, conjointly with the carbon atoms to which they are bonded, form a substituted or unsubstituted, saturated or unsaturated 5-membered or 6-membered ring.

Saturated 5-membered ring systems which are further substituted by methyl, i-propyl or tert-butyl are preferred.

R can also be a group of the formula

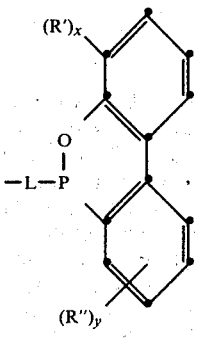

in which R', R", x and y are as defined above. L is a divalent radical and is a substituted or unsubstituted 5-membered or 6-membered ring which contains at least 2 hetero-atoms and which is bonded to the oxaphosphorine radicals via the hetero-atoms, or substituted or unsubstituted aryleneoxy, such as substituted or unsubstituted oxyaryleneoxy or a radical of the formula =N—Z.

If L is an =N—Z grouping, Z is alkyl having 1 to 22, in particular 1 to 16, carbon atoms. Alkyl radicals having 8 to 12 carbon atoms are very particularly suitable. Examples of the radicals can be derived from the listing given in he definitions of $R^1$ and $R^2$. Possible substituents of these radicals are alkoxy having 1 to 4 carbon atoms, carbalkoxy having 2 to 4 carbon atoms or cyano. Z can also be substituted or unsubstituted cycloalkyl which contains 5 or 6, preferably 6, carbon atoms. It can be further substituted by alkyl or alkoxy each having 1 to 4 carbon atoms.

Furthermore, L can be a substituted or unsubstituted 5-membered or 6-membered, saturated or unsaturated ring which contains at least 2 hetero-atoms and which is bonded to the oxaphosphorine radicals via the hetero-atoms. Saturated 5-membered or 6-membered rings which contain 2 nitrogen atoms are preferred, for example:

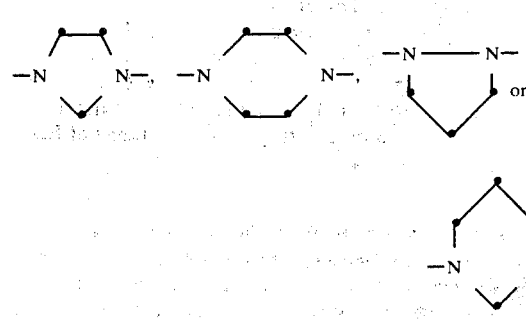

the first two of these being particularly suitable.

All the rings can be substituted by methyl, ethyl, propyl, butyl or tert.-butyl.

L can also be substituted or unsubstituted aryleneoxy. Preferred aryleneoxy radicals are phenyleneoxy or naphthyleneoxy, phenyleneoxy being very particularly suitable. The latter can, like the naphthyleneoxy radical, also be substituted by 1 to 4 further substituents and, for example, can be of the formula

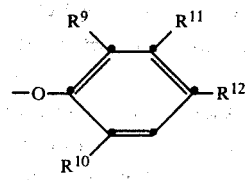

in which $R^9$, $R^{10}$ and $R^{11}$ are as defined above. $R^{21}$, however, is a radical of the formula

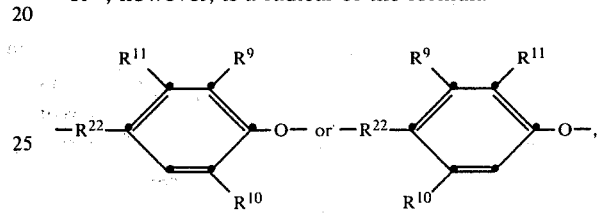

in which $R^{22}$ is —O—, —S— or a group of the formula =$CR^{51}R^{61}$. In the latter, $R^{51}$ and $R^{61}$ independently of one another are hydrogen or alkyl having 1 to 6, in particular 1 to 4, carbon atoms. Groupings of the formula =$CH_2$, =$CHCH_3$ and =$C(CH_3)_2$ are particularly preferred.

$R^9$, $R^{10}$ and $R^{11}$ are as defined above. L can also be one of the following bridge members:

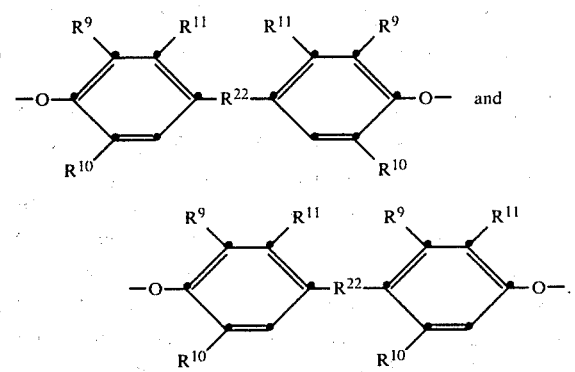

If L is substituted or unsubstituted oxyaryleneoxy, the preferred radicals are oxyphenyleneoxy and oxynaphthyleneoxy. Oxyphenyleneoxy radicals which, like the oxynaphthyleneoxy radicals, can carry 1 or 2 further substituents and are, for example, of the formula

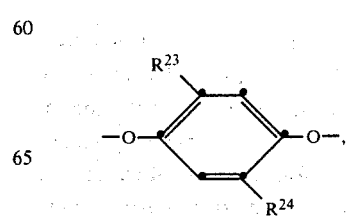

are particularly suitable. In this formula, $R^{23}$ and $R^{24}$ independently of one another are hydrogen or substituted or unsubstituted alkyl having 1 to 18, in particular 1 to 12, carbon atoms. Examples of the alkyl radicals can be derived from the listing of alkyl radicals given in the definitions of $R^1$ and $R^2$. Possible substituents of these radicals are methoxy, halogen, for example chlorine or bromine, and also cyano or nitro. Alkyl radicals having 4 to 8 carbon atoms are very particularly suitable.

$R^{23}$ and $R^{24}$ can also be substituted or unsubstituted alkoxy having 1 to 4 carbon atoms, for example methoxy, propoxy or butoxy, and methoxy is preferred.

The oxyphenyleneoxy radical thus represents bridge members of the formula

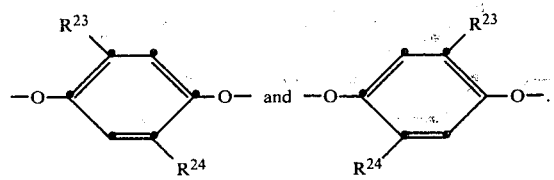

L can also be a radical of the formula $-NB_1-E-NB_2-$. E is an alkylene group having 1 to 8, in particular 1 to 6, carbon atoms. E can also be a group of the formula

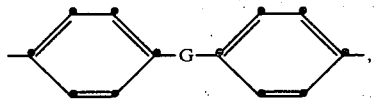

in which G is $-O-$, $-S-$ or an alkylene group of the formula $=CK_1K_2$, in which $K_1$ and $K_2$ independently of one another are hydrogen or alkyl having 1 to 8, in particular 1 to 4, carbon atoms in each case. $=CH_2$, $=CHCH_3$ and $=C(CH_3)_2$ are particularly preferred. $B_1$ and $B_2$ independently of one another are hydrogen or alkyl having 1 to 4 carbon atoms. Methyl and ethyl are preferred. Furthermore, $B_1$ and $B_2$ independently of one another can be the radical A as defined above.

A preferred photographic recording material is now of a type in which the development accelerator is of the formula $$A-R_1 \qquad (4)$$

in which $R_1$ is amino which is unsubstituted or substituted by alkyl, alkenyl, alkynyl, cycloalkyl, aryl or by a heterocyclic radical, substituted or unsubstituted 5-membered or 6-membered cyclic amino, phenoxy which is unsubstituted or substituted by alkyl, alkoxy, carbalkoxy, thioalkyl or carbonamido, or a group of the formula

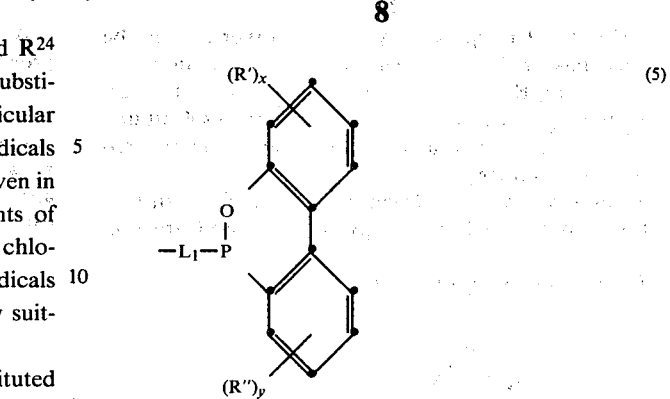

in which $L_1$ is a radical of the formula $=N-Z$, with Z being as defined above, a substituted or unsubstituted 5-membered or 6-membered saturated or unsaturated ring which contains at least 2 hetero-atoms and which is bonded to the oxaphosphorine radicals via the heteroatoms, or substituted or unsubstituted aryleneoxy, substituted or unsubstituted oxyaryleneoxy or a radical of the formula $-NB_3-E_1-NB_4-$, in which $B_3$ and $B_4$ independently of one another are hydrogen, alkyl having 1 to 4 carbon atoms or the radical, A and $E_1$ is alkylene having 1 to 12 carbon atoms or

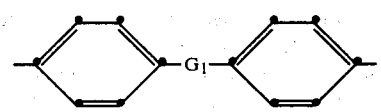

in which $G_1$ is $-O-$, $-S-$ or $=CK_1K_2$, in which $K_1$ and $K_2$ independently of one another are hydrogen or alkyl having 1 to 8 carbon atoms in each case, and in which A, R', R", x and y are as defined above.

A suitable photographic recording material contains a development accelerator of the formula $$A-R_2 \qquad (6)$$

in which $R_2$ is amino which is unsubstituted or substituted by alkyl, alkenyl, alkynyl, cycloalkyl, aryl or by a heterocyclic radical, phenoxy which is unsubstituted or substituted by alkyl, alkoxy, carbalkoxy, thioalkyl or carbonamido or a group of the formula

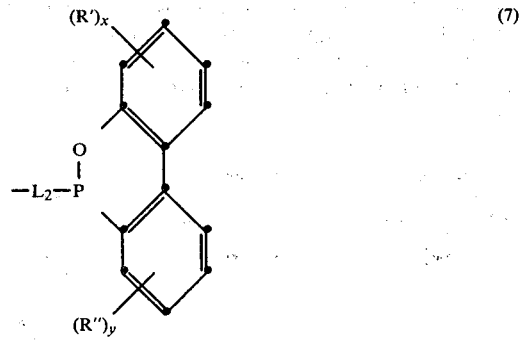

in which $L_2$ is a radical of the formula $=N-Z_1$, in which $Z_1$ is substituted or unsubstituted alkyl having 1 to 22 carbon atoms or substituted or unsubstituted cycloalkyl having 5 or 6 carbon atoms, or $L_2$ is a substituted or unsubstituted 5-membered or 6-membered, saturated or unsaturated ring which contains at least 2 hetero-atoms and which is bonded to the oxaphosphorine radicals via the hetero-atoms, or substituted or unsubstituted aryleneoxy, substituted or unsubstituted oxyaryleneoxy or a radical of the formula —NB$_3$—E$_2$—NB$_4$—, in which E$_2$ is alkylene having 1 to 8 carbon atoms or

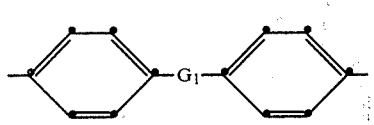

and in which A, R', R'', x, y, B$_3$, B$_4$ and G$_1$ are as defined above.

A photographic recording material is also preferred, which contains a development accelerator of the formula

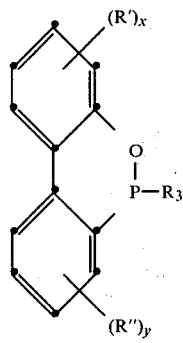
(8)

in which R$_3$ is of the formula

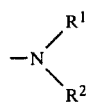
(9)

in which R$^1$ and R$^2$ independently of one another are hydrogen, substituted or unsubstituted alkyl having 1 to 22 carbon atoms, substituted or unsubstituted alkenyl having 2 to 18 carbon atoms, substituted or unsubstituted alkynyl having 2 to 18 carbon atoms, substituted or unsubstituted cycloalkyl having 6 to 8 carbon atoms, substituted or unsubstituted aryl or a substituted or unsubstituted, saturated or unsaturated heterocyclic radical containing at least one nitrogen atom and having 4 or 5 carbon atoms, or in which R$^1$ and R$^2$ conjointly are a divalent radical which forms a 5-membered or 6-membered, substituted or unsubstituted, saturated ring which can contain a further hetero-atom, and R', R'', x and y are as defined above.

A photographic recording material is of interest, wherein the development accelerator is of the formula

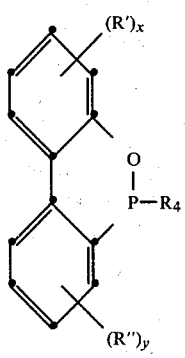
(10)

in which R$_4$ is of the formula

(11)

in which R$^3$ and R$^4$ independently of one another are hydrogen, substituted or unsubstituted alkyl having 1 to 18 carbon atoms, substituted or unsubstituted alkenyl having 2 to 12 carbon atoms, substituted or unsubstituted cycloalkyl having 6 to 8 carbon atoms, substituted or unsubstituted phenyl or a substituted or unsubstituted, saturated or unsaturated heterocyclic radical containing at least one nitrogen atom and having 4 or 5 carbon atoms, or in which R$^3$ and R$^4$ conjointly are a divalent radical which forms a 5-membered or 6-membered, substituted or unsubstituted, saturated ring which can contain a further hetero-atom, and R' and R'', x and y are as defined above.

Particularly preferred photographic material contains a development accelerator of the formula

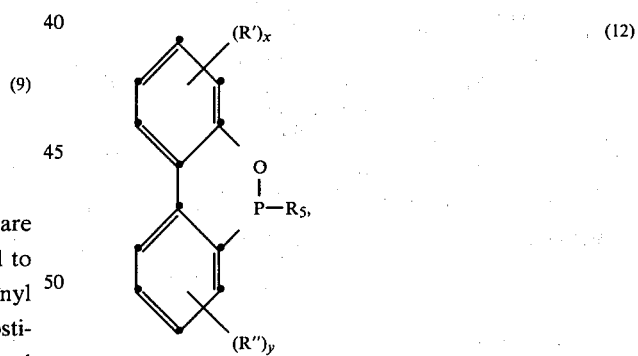
(12)

in which R$_5$ is of the formula

(13)

in which R$^5$ and R$^6$ independently of one another are hydrogen, alkyl having 1 to 18 carbon atoms, alkenyl having 2 to 12 carbon atoms, cycloalkyl having 6 to 8 carbon atoms, phenyl which is unsubstituted or substituted by alkyl having 1 to 6 carbon atoms and which can carry 1, 2 or 3 such alkyl substituents, or are a saturated heterocyclic radical which has 4 or 5 carbon atoms and is unsubstituted or substituted by alkyl having 1 to 4 carbon atoms and contains at least one nitrogen atom and which can carry 1 to 6 such alkyl substituents, or in which $R^5$ and $R^6$ conjointly form a radical of the formula —$(CH_2)_4$—, —$(CH_2)_5$—, —$CH_2CH_2$—O—$CH_2CH_2$— or —$CH_2CH_2$—NT—$CH_2CH_2$—, in which T is hydrogen or alkyl having 1 to 4 carbon atoms, and R', R", x and y are as defined above.

A photographic recording material is also of importance, which contains a development accelerator of the formula

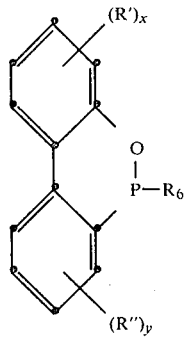

(14)

in which $R_6$ is of the formula

in which $R^7$ and $R^8$ independently of one another are hydrogen, alkyl having 1 to 12 carbon atoms, alkenyl having 2 to 6 carbon atoms, cyclohexyl, cyclooctyl, phenyl which is unsubstituted or substituted by alkyl having 1 to 6 carbon atoms and which can carry 1, 2 or 3 such substituents, or are pyrrolidinyl or piperidinyl which are unsubstituted or substituted by alkyl having 1 to 4 carbon atoms, it being possible for the heterocyclic radicals to carry 1 to 6 such alkyl substituents, or in which $R^7$ and $R^8$ conjointly form a radical of the formula —$(CH_2)_4$—, —$(CH_2)_5$—, —$CH_2CH_2$—O—$CH_2CH_2$— or —$CH_2CH_2$—NH—$CH_2CH_2$—, and R', R", x and y are as defined above.

Particularly suitable photographic recording material contains a development accelerator of the formula

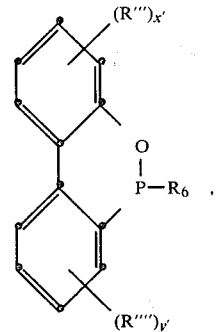

(16)

in which R''' and R'''' independently of one another are hydrogen, methyl, ethyl, chlorine or bromine, x' and y' independently of one another are 0 or 1 and $R_6$ is as defined above.

Moreover, a photographic recording material is of interest, which contains a development accelerator of the formula

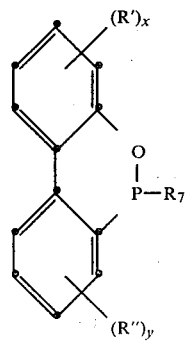

(17)

in which $R_7$ is substituted or unsubstituted phenoxy and R', R", x and y are as defined above.

A valuable photographic recording material contains a development accelerator of the formula

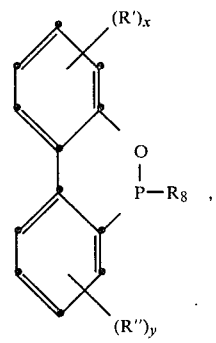

(18)

in which $R_8$ is of the formula

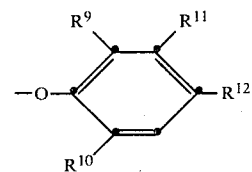

(19)

in which $R^9$ and $R^{10}$ independently of one another are hydrogen or substituted or unsubstituted alkyl having 1 to 12 carbon atoms, $R^{11}$ is hydrogen or substituted or unsubstituted alkyl having 1 to 4 carbon atoms, $R^{12}$ is hydrogen, substituted or unsubstituted alkyl having 1 to 12 carbon atoms, substituted or unsubstituted alkoxy having 1 to 18 carbon atoms, carbalkoxy having 2 to 24 carbon atoms, in which the alkoxy moiety can be further substituted, or is substituted or unsubstituted thioalkyl having 1 to 18 carbon atoms or is of the formula

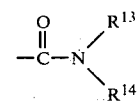

(20)

in which $R^{13}$ and $R^{14}$ independently of one another are hydrogen, substituted or unsubstituted alkyl having 1 to 4 carbon atoms or alkenyl having 3 to 6 carbon atoms, or $R^{12}$ and $R^{11}$ conjointly are those atoms which are required in order to form, together with the carbon atoms to which they are bonded, a substituted or unsubstituted, saturated or unsaturated, 5-membered or 6-membered ring, and R', R'', x and y are as defined above.

A very suitable photographic recording material contains a development accelerator of the formula

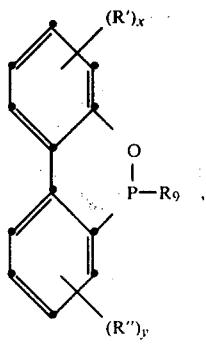
(21)

in which R$_9$ is of the formula

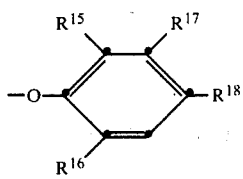
(22)

in which R$^{15}$ and R$^{16}$ independently of one another are hydrogen or alkyl having 1 to 12 carbon atoms, which is unsubstituted or substituted by substituted phenyl, R$^{17}$ is hydrogen or alkyl having 1 to 4 carbon atoms, R$^{18}$ is hydrogen, alkyl having 1 to 12 carbon atoms, which is unsubstituted or substituted by alkoxy having 1 to 18 carbon atoms or by carbalkoxy having 2 to 24 carbon atoms, or is alkoxy having 1 to 12 carbon atoms, carbalkoxy having 2 to 24 carbon atoms, thioalkyl having 1 to 18 carbon atoms or is of the formula

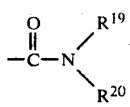
(23)

in which R$^{19}$ and R$^{20}$ independently of one another are hydrogen or alkyl having 1 to 4 carbon atoms, or in which R$^{18}$ and R$^{17}$ conjointly are those atoms which are required in order to form, together with the carbon atoms to which they are bonded, a saturated 5-membered or 6-membered ring which is unsubstituted or substituted by alkyl having 1 to 4 carbon atoms and which can be substituted by up to 4 such alkyl substituents, and R', R'', x and y are as defined as above.

A photographic recording material is of particular interest, which contains a development accelerator of the formula

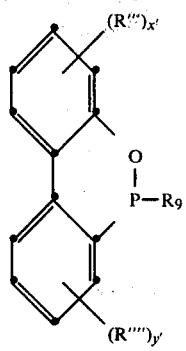
(24)

in which R$_9$, R''', R'''', x' and y' are as defined above.

Moreover, a photographic material is of importance, which contains a development accelerator of the formula

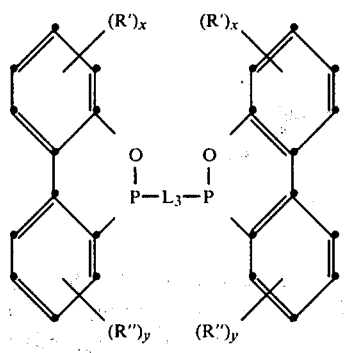
(25)

in which L$_3$ is a radical of the formula =N—Z$_2$, in which Z$_2$ is substituted or unsubstituted alkyl having 1 to 16 carbon atoms or substituted or unsubstituted cyclohexyl, or L$_3$ is substituted or unsubstituted 5-membered or 6-membered, saturated ring which contains at least 2 hetero-atoms and which is bonded to the oxaphosphorine radicals via the hetero-atoms, or L$_3$ is substituted or unsubstituted phenyleneoxy or naphthyleneoxy, or substituted or unsubstituted oxyphenyleneoxy or oxynaphthyleneoxy, and R', R'', x and y are as defined above.

A valuable photographic recording material contains a development accelerator of the formula

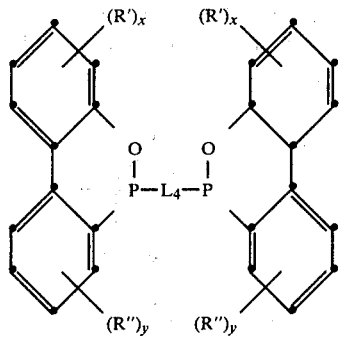
(26)

in which L$_4$ is a radical of the formula =N—Z$_3$ in which Z$_3$ is alkyl having 1 to 16 carbon atoms or cyclohexyl, or L$_3$ is a 5-membered or 6-membered, saturated ring which contains at least 2 nitrogen atoms and which is bonded to the oxaphosphorine radicals via the nitrogen atoms, or $L_4$ is a radical of the formula

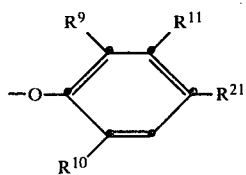
(27)

in which $R^{21}$ is a radical of the formulae

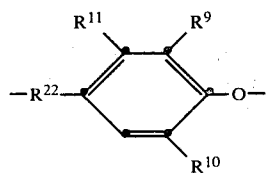
(28)

or

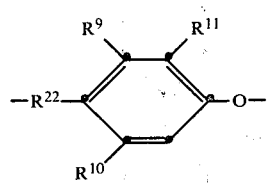
(29)

in which $R^{22}$ is —O—, —S— or $=CR^{51}R^{61}$, in which $R^{51}$ and $R^{61}$ independently of one another are hydrogen or alkyl having 1 to 6 carbon atoms, and $R^9$, $R^{10}$ and $R^{11}$ are as defined above, or $L_4$ is of the formula

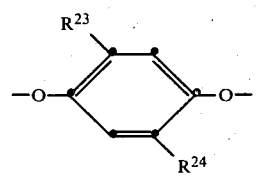
(30)

in which $R^{23}$ and $R^{24}$ independently of one another are hydrogen, substituted or unsubstituted alkyl having 1 to 18 carbon atoms or substituted or unsubstituted alkoxy having 1 to 4 carbon atoms, and R', R'', x and y are as defined above.

An outstandingly suitable photographic recording material contains a development accelerator of the formula

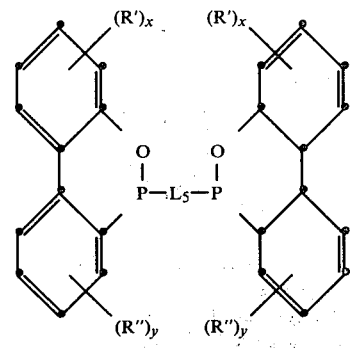
(31)

in which $L_5$ is a radical of the formula $=N—Z_3$, in which $Z_3$ is as defined above, or is a radical of the formulae

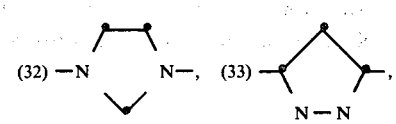

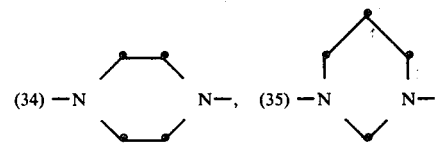

or $L_5$ is of the formula

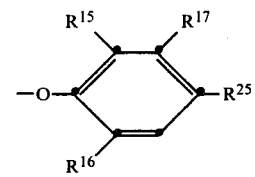
(36)

in which $R^{25}$ is a radical of the formulae

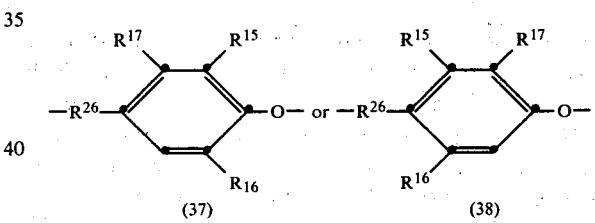
(37)  (38)

in which $R^{26}$ is $=CR^{51}R^{61}$, in which $R^{51}$ and $R^{61}$ are as defined above, and $R^{15}$, $R^{16}$ and $R^{17}$ are as defined above, or $L_5$ is a radical of the formula

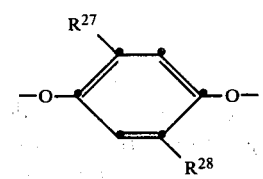
(39)

in which $R^{27}$ and $R^{28}$ independently of one another are hydrogen, alkyl having 1 to 12 carbon atoms or alkoxy having 1 to 4 carbon atoms, and R', R'', x and y are as defined above.

Of particular interest is a photographic recording material which contains a development accelerator of the formula

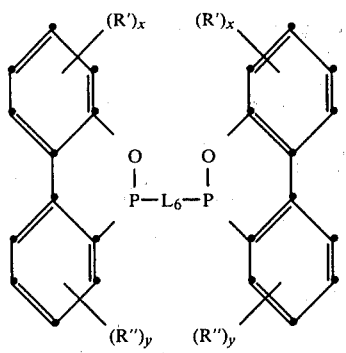
(40)

in which $L_6$ is a radical of the formula $=N-Z_3$, in which $Z_3$ is as defined above, or is a radical of the formulae

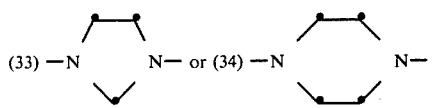

or $L_6$ of the formula

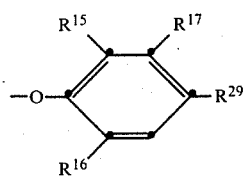
(41)

in which $R^{29}$ is a radical or the formulae

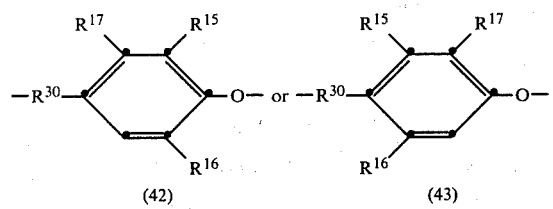
(42)    (43)

in which $R^{30}$ is $=CR^{51}R^{61}$ and $R^{15}$, $R^{16}$ and $R^{17}$ as well as $R^{51}$ and $R^{61}$ are as defined above, or $L_6$ is of the formula

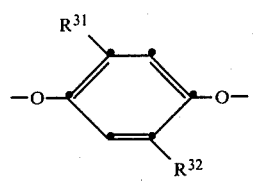
(44)

in which $R^{31}$ and $R^{32}$ independently of one another are hydrogen or alkyl having 1 to 12 carbon atoms, and $R'$, $R''$, x and y are as defined above.

A photographic recording material is of great importance, which contains a development accelerator of the formula

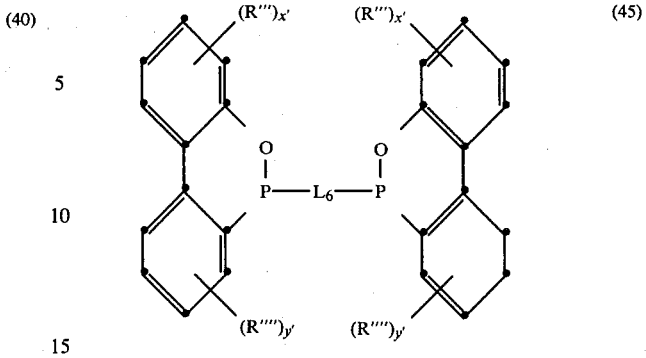
(45)

in which $L_6$, $R'''$, $R''''$, x' and y' are as defined above.

A particularly suitable photographic recording material contains a development accelerator of the formula

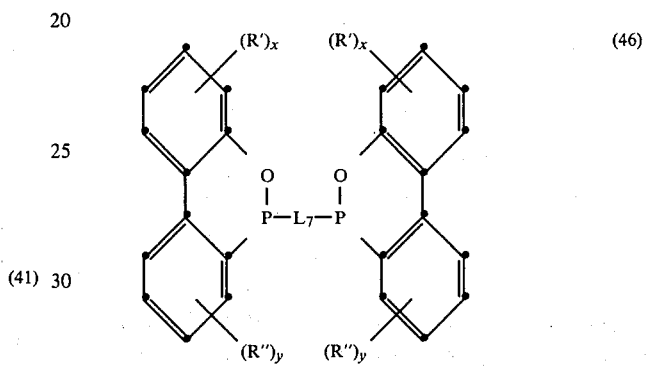
(46)

in which $L_7$ is a radical of the formula $-NB_5-E_3-NB_6-$, in which $B_5$ and $B_6$ independently of one another are hydrogen, methyl, ethyl or the radical A and in which $E_3$ is alkylene having 1 to 6 carbon atoms or

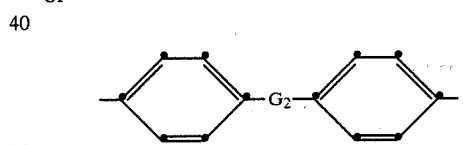

in which $G_2$ is $-O-$, $-S-$ or $=CK_3K_4$, in which $K_3$ and $K_4$ independently of one another are hydrogen or alkyl having 1 to 4 carbon atoms, and $R'$, $R''$, x and y are as defined above.

A preferred photographic recording material contains a development accelerator of the formula

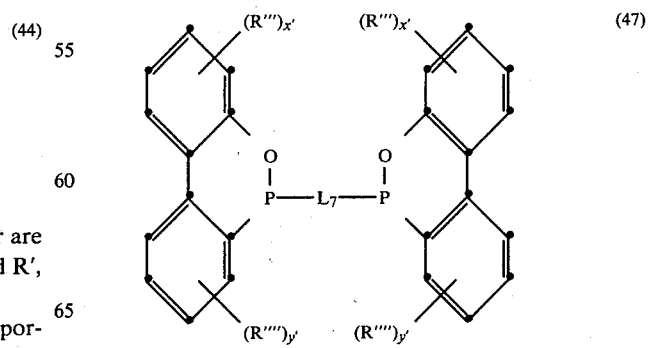
(47)

in which $R'''$, $R''''$, x', y' and $L_7$ are as defined above.

A particularly suitable photographic recording material contains a development accelerator of the formula

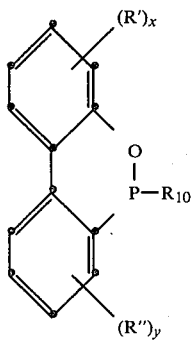 (48)

in which $R_{10}$ is of the formula

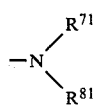 (49)

in which $R^{71}$ is hydrogen, alkyl having 1 to 12 carbon atoms, cyclohexyl or cyclooctyl and $R^{81}$ is alkyl having 1 to 12 carbon atoms, cyclohexyl, cyclooctyl, alkenyl having 2 to 6 carbon atoms, phenyl which is unsubstituted or substituted by alkyl having 1 to 6 carbon atoms and which can carry 1 or 2 such alkyl substituents, or is piperidinyl which is unsubstituted or substituted by alkyl having 1 to 4 carbon atoms and which can carry 1 to 4 such alkyl substituents, or in which $R^{81}$ and $R^{71}$ conjointly form a radical of the formulae $-(CH_2)_4-$, $-(CH_2)_5-$, $-CH_2CH_2-O-CH_2CH_2-$ or $-CH_2CH_2-NH-CH_2CH_2-$, or in which $R_{10}$ is of the formula

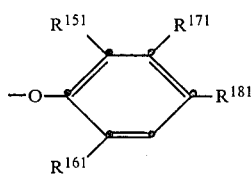 (50)

in which $R^{151}$ and $R^{161}$ independently of one another are hydrogen, alkyl having 1 to 8 carbon atoms, benzyl or phenylethyl, it being possible for the phenyl radicals to be substituted by alkyl having 1 to 4 carbon atoms, $R^{171}$ is hydrogen, methyl or ethyl and $R^{181}$ is hydrogen, alkyl having 1 to 8 carbon atoms, which is unsubstituted or substituted by carbalkoxy having 2 to 24 carbon atoms, or is alkoxy having 1 to 8 carbon atoms or carbalkoxy having 2 to 19 carbon atoms, or $R^{181}$ conjointly with $R^{171}$ represents those atoms which are required in order to form, together with the carbon atoms to which they are bonded, a saturated 5-membered ring which is unsubstituted or substituted by alkyl having 1 to 4 carbon atoms and which can be substituted by up to 4 such alkyl substituents, or in which $R_{10}$ is of the formula

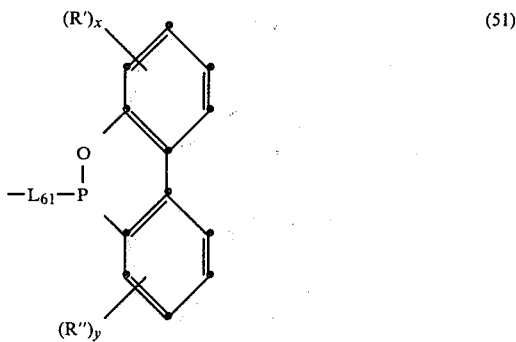 (51)

in which $L_{61}$ is a radical of the formula $=N-Z_4$, in which $Z_4$ is alkyl having 1 to 12 carbon atoms or cyclohexyl, or $L_{61}$ is a radical of the formulae

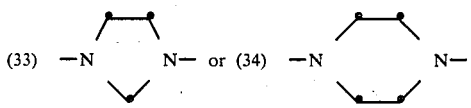

(33) $-N\underset{\diagdown\diagup}{\overset{\diagup\diagdown}{\phantom{X}}}N-$ or (34) $-N\underset{\diagdown\diagup}{\overset{\diagup\diagdown}{\phantom{X}}}N-$ or

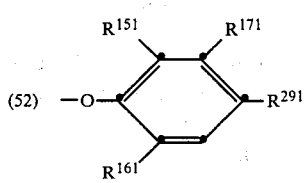 (52)

in which $R^{291}$ is a radical of the formulae

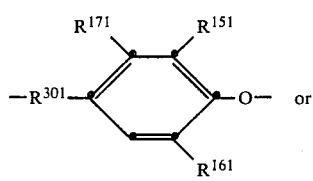 (53)

or

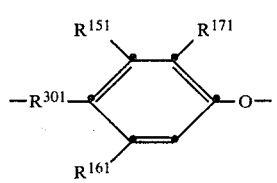 (54)

in which $R^{301}$ is $=CR^{52}R^{62}$, in which $R^{52}$ and $R^{62}$ independently of one another are hydrogen or alkyl having 1 to 4 carbon atoms, or in which $L_{61}$ is of the formula

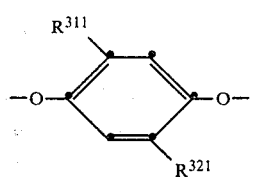 (55)

in which $R^{311}$ and $R^{321}$ independently of one another are hydrogen or alkyl having 1 to 8 carbon atoms, or in which $R_{10}$ is of the formula

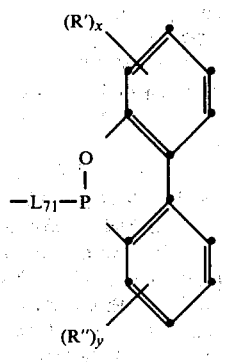 (56)

in which $L_{71}$ is a radical of the formula $-NB_7-E_4-NB_8-$, in which $B_7$ and $B_8$ independently of one another are hydrogen or the radical A, and $E_4$ is alkylene having 1 to 6 carbon atoms or a radical of the formula

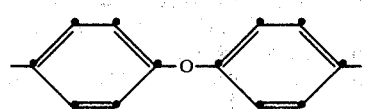

and in which R', R'', x and y are as defined above.

A photographic recording material is also valuable, which contains a development accelerator of the formula

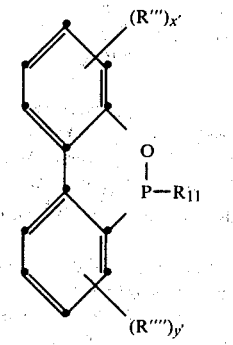 (57)

in which $R_{11}$ is of the formula

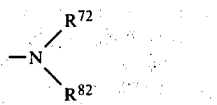 (58)

in which $R^{72}$ is hydrogen, alkyl having 1 to 8 carbon atoms or cyclohexyl and $R^{82}$ is alkyl having 1 to 8 carbon atoms, cyclohexyl, allyl, phenyl which is unsubstituted or substituted by alkyl having 1 to 4 carbon atoms and which can carry 1 or 2 such alkyl substituents, or is piperidin-4-yl which is unsubstituted or substituted by methyl and which can carry 1 to 4 methyl groups, or in which $R^{82}$ and $R^{72}$ conjointly form a radical of the formulae $-(CH_2)_5-$ or $-CH_2CH_2-NH-CH_2CH_2-$, or in which $R_{11}$ is of the formula

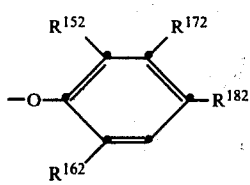 (59)

in which $R^{152}$ and $R^{162}$ independently of one another are hydrogen, alkyl having 1 to 8 carbon atoms or benzyl, wherein the phenyl radical can be substituted by methyl groups, $R^{172}$ is hydrogen or methyl and $R^{182}$ is hydrogen, alkyl having 1 to 8 carbon atoms, alkyl having 1 to 4 carbon atoms, which is substituted by carbalkoxy having 2 to 19 carbon atoms, or is methoxy or carbalkoxy having 2 to 19 carbon atoms, or $R^{182}$ conjointly with $R^{172}$ represents those atoms which are required in order to form, together with the carbon atoms to which they are bonded, a saturated 5-membered ring which is unsubstituted or substituted by 1 to 4 methyl groups, or in which $R_{11}$ is of the formula

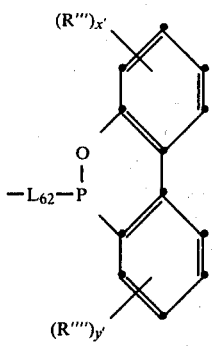 (60)

in which $L_{62}$ is a radical of the formula $=N-Z_4$, with $Z_4$ being as defined above, or is of the formula

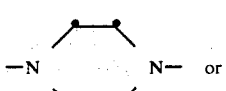 (34)

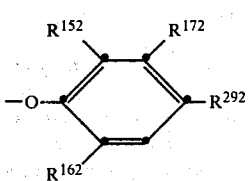 (61)

in which $R^{292}$ is a radical of the formulae

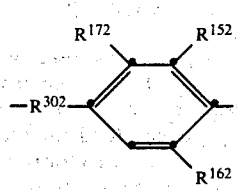 (62)

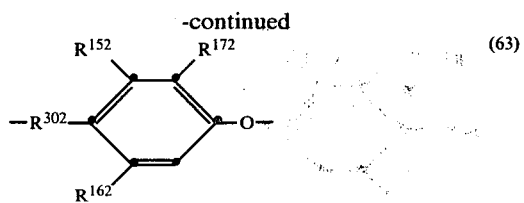

(63)

in which $R^{302}$ is —CH$_2$—, —CHCH$_3$— or —C(CH$_3$)$_2$—, or in which L$_{62}$ is of the formula

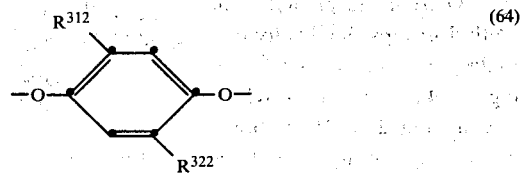

(64)

in which $R^{312}$ and $R^{322}$ independently of one another are hydrogen or alkyl having 1 to 4 carbon atoms, or in which R$_{11}$ is of the formula

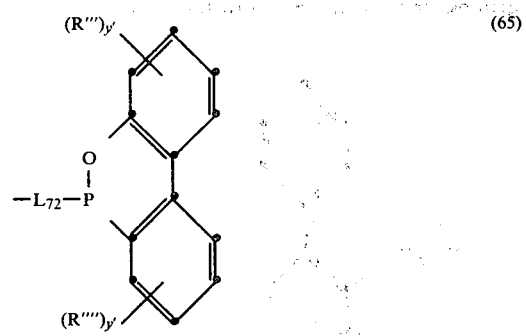

(65)

in which L$_{72}$ is a radical of the formula —NB$_7$—E$_5$—NB$_8$—, in which B$_7$ and B$_8$ are as defined above and E$_5$ is alkylene having 1 to 6 carbon atoms, and in which R''', R'''', x' and y' are as defined above.

The compounds of the formula (1) are known from European Patent Application 352, European Patent Application No. 5,441 and U.S. Pat. No. 4,185,006.

The development accelerators employed according to the invention are used in contact with the silver halide emulsion layer. This means that they must be present in the emulsion layer during development. This can be ensured either by incorporating the compounds into the emulsion layer before exposure, or by making it possible for the compounds to diffuse from a developer to the emulsion layer. This is possible, since the development accelerators are stable to hydrolysis and can therefore be present in the dissolved state in a processing bath for a prolonged period. It is preferred to incorporate the compounds directly into the silver halide emulsion. It is possible to use either aqueous solutions of these compounds or solutions in an organic solvent which does not affect the photographic properties of the light-sensitive material.

The sensitivity-enhancing compounds, used according to the invention, can be added to the emulsion at various points in time during the preparation of the emulsions. For example, they can be added, individually or in admixture with other conventional additives, during the physical or chemical ripening or at any other point in time before coating of the emulsion. Most preferably, however, this is carried out after chemical ripening and shortly before coating of the emulsion.

The quantity added depends on the compound selected and on the type of colloidal binder used for the silver halide emulsion. In general, the compounds according to the present invention are used in a quantity of 1 to 50 g per mol of silver halide.

The conventional methods can be used for incorporating the compounds into the silver halide emulsions. For example, solutions in high-boiling solvents, which are hardly miscible with water, for example di-n-butyl phthalate and tricresyl phosphate, or in lower-boiling solvents, which are hardly miscible with water, such as ethyl acetate, methylene chloride and chloroform, and the like, or mixtures thereof can be used for incorporation. For this purpose, these solutions are dispersed in extremely fine droplets, preferably in the presence of a wetting agent or dispersant, in a hydrophilic colloidal medium. The low-boiling solvent which hardly mixes with water is then evaporated off. Of course, any other technique known to those skilled in the art for incorporating additives into colloid mixtures can be applied. For example, water-soluble substances which contain a sulfo group (in the acid form or salt form) conferring solubility in water can be incorporated from an aqueous or alkaline solution into the coating composition for the particular layer.

The hydrophilic colloid composition in which the compounds according to the invention are dispersed or dissolved does not absolutely have to be the coating composition for the silver halide emulsion layer itself, which should contain them. Advantageously, the compounds can initially be dispersed or dissolved in an aqueous, light-insensitive, hydrophilic colloid solution, whereupon the resulting mixture, if appropriate after removal of the organic solvents, is intimately mixed with the coating composition for the light-sensitive silver halide emulsion layer shortly before application.

Thus, for example, polymeric or copolymeric latices can be charged with the compounds according to the invention, if appropriate in the presence of an organic solvent. The mixture thus obtained is then admixed to the light-sensitive silver halide emulsion before application.

Owing to their property of assisting the developability of photographic layers, the compounds used according to the invention are outstandingly suitable for increasing the X-ray light-sensitivity and the general light-sensitivity of orthochromatic, panchromatic and other special emulsions as well as of conventional emulsions which are not spectrally sensitised. The substances can be added to these emulsions either separately or together with the conventional sensitising dyes. It should also be mentioned that the advantages of the compounds used according to the invention, as described, are applicable to both negative emulsions and positive emulsions.

The new compounds are advantageous for the development of light-sensitive materials which are intended for the reproduction of graphical illustrations.

In the silver dye bleach process in which, after a first black-and-white development, the incorporated dye is, with the aid of the silver image formed, bleached imagewise proportionally to the quantity of silver, the compounds according to the invention have proved very particularly suitable. In their presence, considerably larger quantities of silver are developed after exposure of the material, and this manifests itself subsequently in a better and more complete bleaching of the dye. Due to the better utilisation of the silver coated in, it is also possible to save quite considerable quantities of silver.

The developer substances known to those skilled in the art can be used as the developer. The processing corresponds to the methods conventionally used for the corresponding photographic material.

The preparation of the development accelerators used according to the invention is known from the literature quoted. It is explained in more detail in the examples which follow.

EXAMPLE 1

35.1 g (0.15 mol) of 6-chloro-dibenzo[c,e][1,2]oxaphosphorine, 27.1 g (0.15 mol) of dicyclohexylamine and 50 ml of triethylamine are kept for 10 hours at reflux temperature. Toluene is added to the solution, the triethylamine hydrochloride is removed by filtration, and the filtrate is concentrated in vacuo. The crystalline product has a melting point of 162° C. (compound 4 in Table 1).

EXAMPLE 2

Following the procedure as described in Example 1 and using 15.1 g (0.15 mol) of diisopropylamine instead of the dicyclohexylamine, 6-(N,N-di-isopropylamino)-dibenzo[c,e][1,2]oxaphosphorine having a melting point of 111° C. is obtained. (Compound 5 in Table 1).

EXAMPLE 3

Using one mol-equivalent of cyclohexylamine and two mol-equivalents of 6-chloro-dibenzo[c,e][1,2]oxaphosphorine under conditions otherwise identical to those described in Example 1, N,N-bis-(dibenzo[c,e][1,2]oxaphosphorin-6-yl)-N-cyclohexylamine having a melting point of 191° C. is obtained (compound 10 in Table 1).

The compounds listed in Table 1 are obtained analogously.

TABLE 1

| No. | Compound |
| --- | --- |
| 1 | 6-(N,N—Di-n-octylamino)-dibenzo[c,e][1,2]oxaphosphorine |
| 2 | 6-(N—2',6'-Di-t-butylphenylamino)-dibenzo[c,e][1,2]oxaphosphorine |
| 3 | 6-(N—Cyclohexyl-N—allyl-amino)-dibenzo[c,e][1,2]oxaphosphorine |
| 4 | 6-(N,N—Di-cyclohexylamino)-dibenzo[c,e][1,2]oxaphosphorine |
| 5 | 6-(N,N—Di-isopropylamino)-dibenzo[c,e][1,2]oxaphosphorine |
| 6 | 1,4-Bis-(dibenzo[c,e][1,2]oxaphosphorin-6'-yl)-piperazine |
| 7 | 6-[N—Dodecyl-N—4'-(2',2',6',6'-tetramethylpiperidinyl)-amino]-dibenzo[c,e][1,2]oxaphosphorine |
| 8 | N,N—Bis-(dibenzo[c,e][1,2]oxaphosphorin-6-yl)-N—n-decylamine |
| 9 | N,N,N',N'—Tetra-(dibenzo[c,e][1,2]oxaphosphorin-6-yl)-hexamethylenediamine |
| 10 | N,N—Bis-(dibenzo[c,e][1,2]oxaphosphorin-6-yl)-cyclohexylamine |
| 11 | N,N—Bis-(dibenzo[c,e][1',2']oxaphosphorin-6'-yl)-2-ethyl-n-hexylamine |
| 12 | 6-(2,6-Di-tert-butyl-phenoxy)-dibenzo[c,e][1,2]oxaphosphorine |
| 13 | 6-(2,4-Di-tert-octyl-phenoxy)-dibenzo[c,e][1,2]oxaphosphorine |
| 14 | 6-(2,4-Di-tert-amyl-phenoxy)-dibenzo[c,e][1,2]oxaphosphorine |
| 15 | 6-(2,6-Di-tert-butyl-4-methoxy-phenoxy)-dibenzo[c,e][1,2]oxaphosphorine |
| 16 | 6-(1',1',3',3'-Tetramethyl-6'-tert.-butyl-5'-indanoxy)-dibenzo[c,e][1,2]oxaphosphorine |

TABLE 1-continued

| No. | Compound |
| --- | --- |
| 17 | 6-[2',6'-Di-tert.-butyl-4'-(2'-n-octadecyloxycarbonyl-ethyl)-phenoxy]-dibenzo[c,e][1,2]oxaphosphorine |
| 18 | 6-(2',4',6'-Tri-tert.-butyl-phenoxy)-dibenzo[c,e][1,2]oxaphosphorine |
| 19 | 6-(2',6'-Di-tert.-butyl-4'-n-octadecyloxycarbonyl-phenoxy)-dibenzo[c,e][1,2]oxaphosphorine |
| 20 | 6-(2,4-Di-4-dimethylbenzylphenoxy)-dibenzo[c,e][1,2]oxaphosphorine |
| 21 | 2',4'-Di-tert.-butyl-hydroquinone-(dibenzo[c,e][1,2]oxaphosphorin-6-yl)ether |
| 22 | 6-(2,6-Dicyclopentyl-4-tert.-butyl)-dibenzo[c,e][1,2]oxaphosphorine |
| 23 | 6-(2,6-Diphenyl-4-dodecyloxy)-dibenzo[c,e][1,2]oxaphosphorine |

EXAMPLE 4

The quantities of development accelerator, indicated in Table 2 which follows, are in each case dissolved in a mixture of 534 mg of tricresyl phosphate and 20 ml of ethyl acetate. 140 ml of an aqueous 6% gelatine solution and 1 ml of a 0.8% solution of diisobutylnaphthalenesulfonic acid (sodium salt) are added to the first solution.

The mixture is emulsified for 5 minutes by means of an ultrasonic apparatus. To this mixture, a silver halide emulsion having a total silver content of 0.6 g of silver, and an aqueous solution of the hardener of the formula

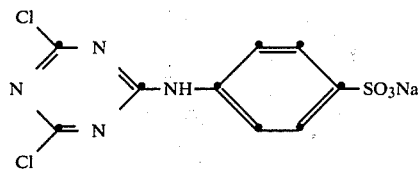

are added.

The mixture is coated at ~40° C. on polyethylene-coated paper and is dried at room temperature.

The coated paper samples thus obtained are exposed for 2 seconds under a 21-step wedge ($\Delta=0.15$) with 200 lux and are then processed at 30° C. as follows:

3 minutes developing
1 minute washing
3 minutes fixing
4 minutes washing, followed by drying.

The processing baths used have the conventional compositions known in photography.

Black-and-white images of the wedge, which have the characteristic data described in Table 2, are obtained.

TABLE 2

| Sample | Development accelerator No. | Quantities coated in, in g | Measured grey densities at step x · | | | | |
| --- | --- | --- | --- | --- | --- | --- | --- |
| | | | 1 | 4 | 8 | 12 | 16 |
| 1 | — | — | 70 | 54 | 21 | 1 | 0 |
| 2 | 4 | 0.129 | 80 | 65 | 34 | 6 | 1 |
| 3 | 13 | 0.176 | 85 | 73 | 41 | 8 | 1 |

This shows clearly that, over the entire exposure range, higher silver densities are obtained in the presence of the oxaphosphorines, with the same development.

EXAMPLE 5

Coatings corresponding to Example 4 are prepared, except that the development accelerators indicated in Table 3 are used. The samples are exposed for two seconds under a 5-step wedge with 200 lux and processed as in Example 4. The developed, metallic silver on the individual steps is determined by X-ray fluorimetry. The results obtained are compiled in Table 3.

TABLE 3

| Sample No. | Development accelerator | Quantity coated in, in g | Measured quantity of silver in mg . m$^{-2}$ on step | | | |
|---|---|---|---|---|---|---|
| | | | 1 | 2 | 3 | 4 |
| 1 | — | — | 140 | 266 | 328 | 338 |
| 2 | 8 | 0.189 | 310 | 406 | 446 | 449 |
| 3 | 17 | 0.190 | 235 | 327 | 346 | 388 |

With addition of the oxaphosphorines, larger quantities of silver were measured on all steps, under the same development conditions.

EXAMPLE 6

0.427 mmol of the development accelerator No. 13 0.32 mmol of the dye of the formula

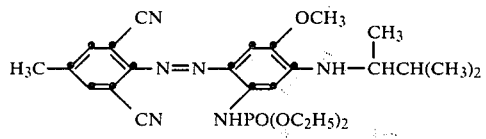

are dissolved in a mixture of 2.5 g of tricresyl phosphate and 25 ml of ethyl acetate. 8.5 g of gelatine in the form of a 6% aqueous solution and 1.0 ml of a 0.8% solution of a wetting agent of the formula

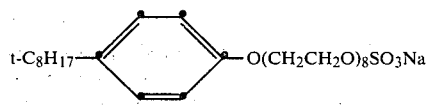

are added and the mixture is emulsified for 5 minutes by means of an ultrasonic apparatus. A silver halide emulsion having a silver content of 0.75 g and an aqueous solution of the hardener of the formula

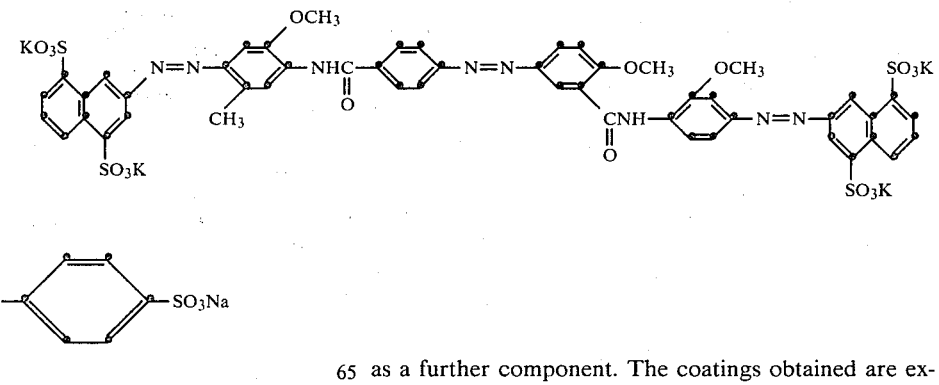

are added to the freshly prepared emulsion containing the dye and development accelerator.

The mixture is adjusted to a pH value of 6.5 and is coated at 40° C. on polyethylene-coated paper. After the layer has solidified, the whole is dried at room temperature.

Samples which, however, contain equimolar quantities of the development accelerator No. 10 in place of the additive No. 13 are coated in the same way. As a control, one sample is prepared without an addition of accelerator.

These samples are exposed for 2 seconds under a 21-step wedge with 500 lux and are processed at 30° C. as follows:
1. Development—3 minutes
2. Washing—1 minute
3. Dye bleach—3 minutes
4. Washing—1 minute
5. Fixing—3 minutes
6. Washing—4 minutes The processing baths 1. and 5. have the same composition as in Example 1. The dye bleach bath 3. is composed as follows:
1,950 ml of water
56 ml of concentrated H$_2$SO$_4$
2 ml of mercaptosuccinic acid
18 g of NaI
12 g of the disodium salt of 4-nitrophenol-2-sulfonic acid
2 g of 6-methoxy-2,3-dimethyl-quinoxaline Clear, sharp magenta wedges having an absorption maximum at 564 nm and the densities indicated in Table 4 are obtained.

TABLE 4

| Sample No. | Development accelerator | Quantity in g | Dye density × 100, measured on step | | | | | | | |
|---|---|---|---|---|---|---|---|---|---|---|
| | | | 1 | 2 | 4 | 6 | 8 | 10 | 12 | 20 |
| 1 | — | — | 18 | 21 | 29 | 80 | 173 | 217 | 230 | 231 |
| 2 | 10 | 0.170 | 12 | 12 | 12 | 12 | 25 | 106 | 178 | 210 |
| 3 | 13 | 0.176 | 13 | 13 | 13 | 15 | 64 | 152 | 205 | 220 |

This comparison shows that, with an addition of development accelerator, the coated-in dye is bleached to a greater extent over the entire exposure range, due to greater quantities of silver.

EXAMPLE 7

Analogously to Example 4, coatings are prepared which, however, also contain the dye of the formula as a further component. The coatings obtained are exposed and processed in accordance with Example 6. Clear, sharp yellow wedges are obtained. The measured densities are compiled in Table 5.

TABLE 5

| Sample No. | Development accelerator | Quantity used in mg | Density × 100, measured on step | | | | | | |
|---|---|---|---|---|---|---|---|---|---|
| | | | 1 | 3 | 6 | 9 | 12 | 15 | 20 |
| 1 | — | — | 9 | 12 | 47 | 193 | 251 | 274 | 257 |
| 2 | 13 | 176 | 9 | 10 | 13 | 57 | 198 | 240 | 237 |
| 3 | 10 | 170 | 8 | 8 | 11 | 56 | 184 | 230 | 233 |
| 4 | 8 | 190 | 9 | 9 | 9 | 32 | 156 | 210 | 226 |

The substantially more complete dye bleach (lower colour densities) in the samples containing the development accelerators is clearly evident.

EXAMPLE 8

0.108 g of the development accelerator No. 10 is dissolved in a mixture of 20 ml of ethyl acetate and 534 mg of tricresyl phosphate. This solution is emulsified, in accordance with Example 4, in an aqueous gelatine solution in the presence of a wetting agent of the formula

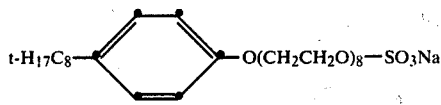

The emulsion obtained is coated, together with a silver bromide gelatine emulsion, on a triacetate base. The coating weight is 3 g/m² of gelatine, 4.5 g/m² of silver and 54 mg/m² of development accelerator (Sample A).

Two further samples are prepared as described; one of these, however, does not contain any development accelerator or tricresyl phosphate (Sample B), and the other does not contain any development accelerator but does contain tricresyl phosphate (Sample C).

The Samples A, B and C are exposed and processed in accordance with Example 4. Measurement of the steps obtained gives the following sensitometric data:

TABLE 6:

| Sample | $S_{2.0}$ (log E)* | Fog |
|---|---|---|
| A | 2.50 | 0.05 |
| B | 2.31 | 0.05 |
| C | 2.34 | 0.05 |

*measured as density 2 + fog

These results show that, without promoting fogging, the material containing the development accelerator has 1.5 times the sensitivity of the corresponding materials without an accelerator.

Similar results are obtained when other conventional silver halide emulsions, for example silver chloride emulsions, silver chlorobromide emulsions or silver bromoiodide emulsions, are used.

What is claimed is:

1. A photographic recording material, which contains at least one development accelerator in at least one silver halide emulsion layer or in a colloid layer adjacent to the silver halide emulsion layer, wherein the development accelerator is of the formula

A—R     (1)

in which A is a dibenzo[c,e][1,2]oxaphosphorine radical of the formula

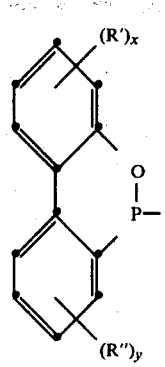

in which R' and R" independently of one another are hydrogen, substituted or unsubstituted alkyl having 1 to 4 carbon atoms or halogen, x and y independently of one another are 0, 1, 2 or 3 and R is substituted or unsubstituted amino, substituted or unsubstituted cyclic amino, substituted or unsubstituted aryloxy or a group of the formula

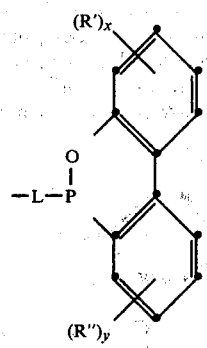

in which L is a radical of the formula =N—Z, with Z being substituted or unsubstituted alkyl or cycloalkyl, or a substituted or unsubstituted 5-membered or 6-membered, saturated or unsaturated ring which contains at least 2 hetero-atoms and which is bonded to the oxaphosphorine radicals via the hetero-atoms, or substituted or unsubstituted aryleneoxy, substituted or unsubstituted oxyaryleneoxy or a radical of the formula —NB₁—E—NB₂, in which B₁ and B₂ independently of one another are hydrogen, alkyl or the radical A and E is alkylene or

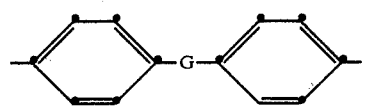

in which G is —O—, —S— or alkylene, and R', R", x and y are as defined above.

2. A photographic recording material according to claim 1, wherein the development accelerator is of the formula

A—R₁     (4)

in which R₁ is amino which is unsubstituted or substituted by alkyl, alkenyl, alkynyl, cycloalkyl, aryl or by a heterocyclic radical, substituted or unsubstituted 5-membered or 6-membered cyclic amino, phenoxy which is unsubstituted or substituted by alkyl, alkoxy, carbalkoxy, thioalkyl or carbonamido, or a group of the formula

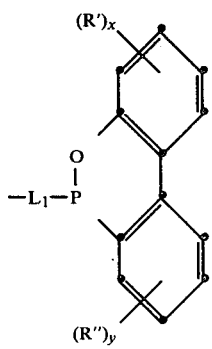

in which $L_1$ is a radical of the formula $=N-Z$, with Z being as defined in claim 1, a substituted or unsubstituted 5-membered or 6-membered saturated or unsaturated ring which contains at least 2 hetero-atoms and which is bonded to the oxaphosphorine radicals via the hetero-atoms, or substituted or unsubstituted aryleneoxy, substituted or unsubstituted oxyaryleneoxy or a radical of the formula $-NB_3-E_1-NB_4-$, in which $B_3$ and $B_4$ independently of one another are hydrogen, alkyl having 1 to 4 carbon atoms or the radical A, and $E_1$ is alkylene having 1 to 12 carbon atoms or a radical of the formula

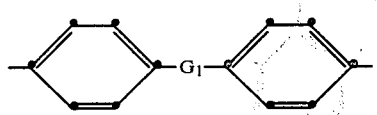

in which $G_1$ is $-O-$, $-S-$ or $=CK_1K_2$, in which $K_1$ and $K_2$ independently of one another are hydrogen or alkyl having 1 to 8 carbon atoms in each case, and in which A, R', R", x and y are as defined in claim 1.

3. A photographic recording material according to claim 2, wherein the development accelerator is of the formula $$A-R_2 \qquad (6)$$

in which $R_2$ is amino which is unsubstituted or substituted by alkyl, alkenyl, alkynyl, cycloalkyl, aryl or by a heterocyclic radical, phenoxy which is unsubstituted or substituted by alkyl, alkoxy, carbalkoxy, thioalkyl or carbonamido or a group of the formula

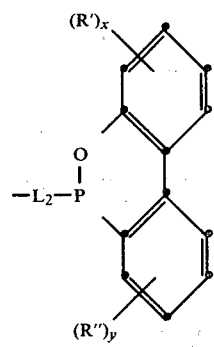

in which $L_2$ is a radical of the formula $=N-Z_1$, in which $Z_1$ is substituted or unsubstituted alkyl having 1 to 22 carbon atoms or substituted or unsubstituted cycloalkyl having 5 or 6 carbon atoms, or $L_2$ is a substituted or unsubstituted 5-membered or 6-membered, saturated or unsaturated ring which contains at least 2 hetero-atoms and which is bonded to the oxaphosphorine radicals via the hetero-atoms, or substituted or unsubstituted aryleneoxy, substituted or unsubstituted oxyaryleneoxy or a radical of the formula $-NB_3-E_2-NB_4-$, in which $E_2$ is alkylene having 1 to 8 carbon atoms or

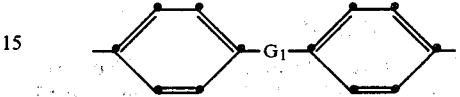

and in which A, R', R", x, y, $B_3$, $B_4$ and $G_1$ are as defined in claim 2.

4. A photographic recording material according to claim 3, characterised in that the development accelerator is of the formula

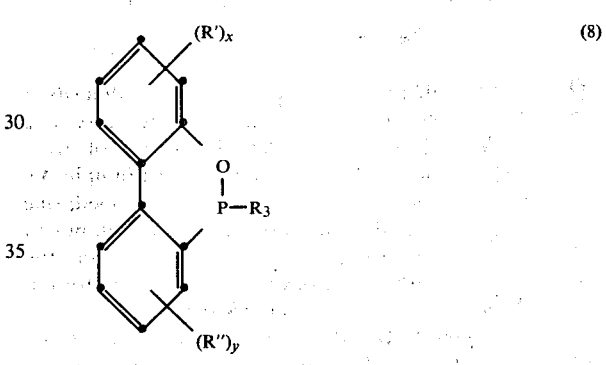

in which $R_3$ is of the formula

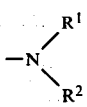

in which $R^1$ and $R^2$ independently of one another are hydrogen, substituted or unsubstituted alkyl having 1 to 22 carbon atoms, substituted or unsubstituted alkenyl having 2 to 18 carbon atoms, substituted or unsubstituted alkynyl having 2 to 18 carbon atoms, substituted or unsubstituted cycloalkyl having 6 to 8 carbon atoms, substituted or unsubstituted aryl or a substituted or unsubstituted, saturated or unsaturated heterocyclic radical containing at least one nitrogen atom and having 4 or 5 carbon atoms, or in which $R^1$ and $R^2$ conjointly are a divalent radical which forms a 5-membered or 6-membered, substituted or unsubstituted, saturated ring which can contain a further hetero-atom, and R', R", x and y are as defined in claim 3.

5. A photographic recording material according to claim 4, wherein the development accelerator is of the formula

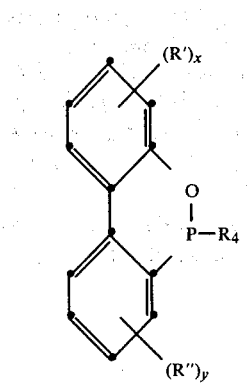

(10)

in which R₄ is of the formula

(11)

in which R³ and R⁴ independently of one another are hydrogen, substituted or unsubstituted alkyl having 1 to 18 carbon atoms, substituted or unsubstituted alkenyl having 2 to 12 carbon atoms, substituted or unsubstituted cycloalkyl having 6 to 8 carbon atoms, substituted or unsubstituted phenyl or a substituted or unsubstituted, saturated or unsaturated heterocyclic radical containing at least one nitrogen atom and having 4 or 5 carbon atoms, or in which R³ and R⁴ conjointly are a divalent radical which forms a 5-membered or 6-membered, substituted or unsubstituted, saturated ring which can contain a further hetero-atom, and R' and R", x and y are as defined in claim 4.

6. A photographic recording material according to claim 5, wherein the development accelerator is of the formula

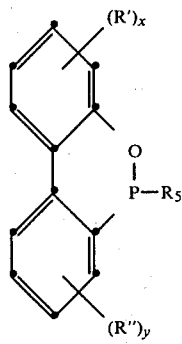

(12)

in which R₅ is of the formula

(13)

in which R⁵ and R⁶ independently of one another are hydrogen, alkyl having 1 to 18 carbon atoms, alkenyl having 2 to 12 carbon atoms, cycloalkyl having 6 to 8 carbon atoms, phenyl which is unsubstituted or substituted by alkyl having 1 to 6 carbon atoms and which can carry 1, 2 or 3 such alkyl substituents, or are a saturated heterocyclic radical which has 4 or 5 carbon atoms and is unsubstituted or substituted by alkyl having 1 to 4 carbon atoms and contains at least one nitrogen atom and which can carry 1 to 6 such alkyl substituents, or in which R⁵ and R⁶ conjointly form a radical of the formula —(CH₂)₄—, —(CH₂)₅—, —CH₂CH₂—O—CH₂CH₂— or —CH₂CH₂—NT—CH₂CH₂—, in which T is hydrogen or alkyl having 1 to 4 carbon atoms, and R', R", x and y are as defined in claim 5.

7. A photographic recording material according to claim 6, wherein the development accelerator is of the formula

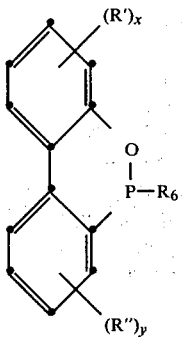

(14)

in which R₆ is of the formula

in which R⁷ and R⁸ independently of one another are hydrogen, alkyl having 1 to 12 carbon atoms, alkenyl having 2 to 6 carbon atoms, cyclohexyl, cyclooctyl, phenyl which is unsubstituted or substituted by alkyl having 1 to 6 carbon atoms and which can carry 1, 2 or 3 such substituents, or are pyrrolidinyl or piperidinyl which are unsubstituted or substituted by alkyl having 1 to 4 carbon atoms, it being possible for the heterocyclic radicals to carry 1 to 6 such alkyl substituents, or in which R⁷ and R⁸ conjointly form a radical of the formula —(CH₂)₄—, —(CH₂)₅—, —CH₂CH₂—O—CH₂CH₂— or —CH₂CH₂—NH—CH₂CH₂—, and R', R", x and y are as defined in claim 6.

8. A photographic recording material according to claim 7, wherein the development accelerator is of the formula

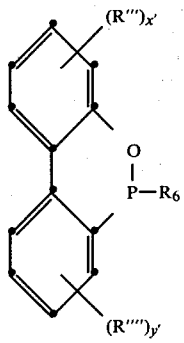

(16)

in which R'" and R"" independently of one another are hydrogen, methyl, ethyl, chlorine or bromine, x' and y' independently of one another are 0 or 1 and $R_6$ is as defined in claim 7.

9. A photographic recording material according to claim 3, wherein the development accelerator is of the formula

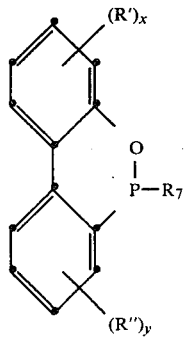
(17)

in which $R_7$ is substituted or unsubstituted phenoxy and R', R", x and y are as defined in claim 7.

10. A photographic recording material according to claim 9, wherein the development accelerator is of the formula

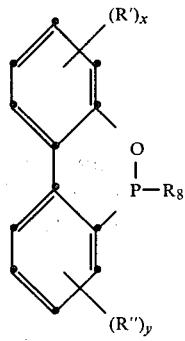
(18)

in which $R_8$ is of the formula

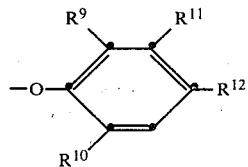
(19)

in which $R^9$ and $R^{10}$ independently of one another are hydrogen or substituted or unsubstituted alkyl having 1 to 12 carbon atoms, $R^{11}$ is hydrogen or substituted or unsubstituted alkyl having 1 to 4 carbon atoms, $R^{12}$ is hydrogen, substituted or unsubstituted alkyl having 1 to 12 carbon atoms, substituted or unsubstituted alkoxy having 1 to 18 carbon atoms, carbalkoxy having 2 to 24 carbon atoms, in which the alkoxy moiety can be further substituted, or is substituted or unsubstituted thioalkyl having 1 to 18 carbon atoms or is of the formula

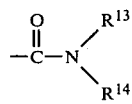
(20)

in which $R^{13}$ and $R^{14}$ independently of one another are hydrogen, substituted or unsubstituted alkyl having 1 to 4 carbon atoms or alkenyl having 3 to 6 carbon atoms, or $R^{12}$ and $R^{11}$ conjointly are those atoms which are required in order to form, together with the carbon atoms to which they are bonded, a substituted or unsubstituted, saturated or unsaturated, 5-membered or 6-membered ring, and R', R", x and y are as defined in claim 9.

11. A photographic recording material according to claim 10, wherein the development accelerator is of the formula

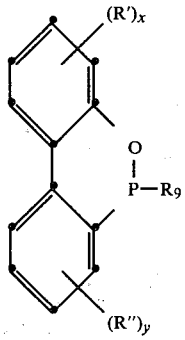
(21)

in which $R_9$ is of the formula

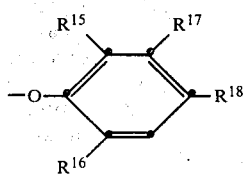
(22)

in which $R^{15}$ and $R^{16}$ independently of one another are hydrogen or alkyl having 1 to 12 carbon atoms, which is unsubstituted or substituted by substituted phenyl, $R^{17}$ is hydrogen or alkyl having 1 to 4 carbon atoms, $R^{18}$ is hydrogen, alkyl having 1 to 12 carbon atoms, which is unsubstituted or substituted by alkoxy having 1 to 18 carbon atoms or by carbalkoxy having 2 to 24 carbon atoms, or is alkoxy having 1 to 12 carbon atoms, carbalkoxy having 2 to 24 carbon atoms, thioalkyl having 1 to 18 carbon atoms or is of the formula

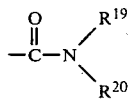
(23)

in which $R^{19}$ and $R^{20}$ independently of one another are hydrogen or alkyl having 1 to 4 carbon atoms, or in which $R^{18}$ and $R^{17}$ conjointly are those atoms which are required in order to form, together with the carbon atoms to which they are bonded, a saturated 5-membered or 6-membered ring which is unsubstituted or substituted by alkyl having 1 to 4 carbon atoms and which can be substituted by up to 4 such alkyl substituents, and R', R", x and y are as defined in claim 10.

12. A phorographic recording material according to claim 11, wherein the above development accelerator is of the formula

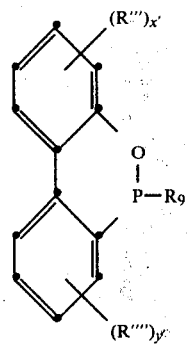
(24)

in which $R_9$, $R'''$, $R''''$, $x'$ and $y'$ are as defined in claim 8, and $R^8$ is as defined in claim 11.

13. A photographic recording material according to claim 3, wherein the development accelerator is of the formula

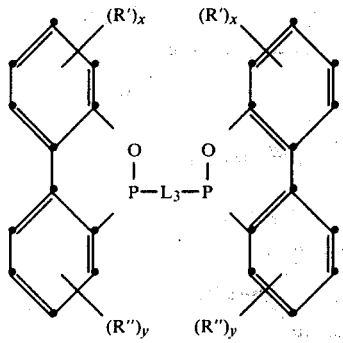
(25)

in which $L_3$ is a radical of the formula $=N-Z_2$, in which $Z_2$ is substituted or unsubstituted alkyl having 1 to 16 carbon atoms or substituted or unsubstituted cyclohexyl, or $L_3$ is a substituted or unsubstituted 5-membered or 6-membered, saturated ring which contains at least 2 hetero-atoms and which is bonded to the oxaphosphorine radicals via the hetero-atoms, or $L_3$ is substituted or unsubstituted phenyleneoxy or naphthyleneoxy, or substituted or unsubstituted oxyphenyleneoxy or oxynaphthyleneoxy, and $R'$, $R''$, x and y are as defined in claim 11.

14. A photographic recording material according to claim 13, wherein the development accelerator is of the formula

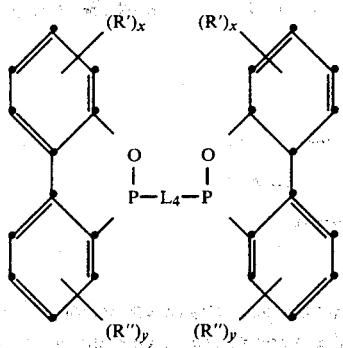
(26)

in which $L_4$ is a radical of the formula $=N-Z_3$ in which $Z_3$ is alkyl having 1 to 16 carbon atoms or cyclohexyl, or $L_3$ is a 5-membered or 6-membered, saturated ring which contains at least 2 nitrogen atoms and which is bonded to the oxaphosphorine radicals via the nitrogen atoms, or $L_4$ is a radical of the formula

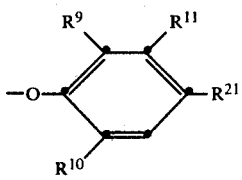
(27)

in which $R^{21}$ is a radical of the formula

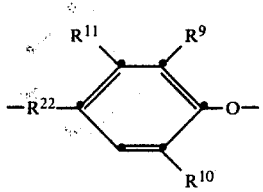
(28)

or

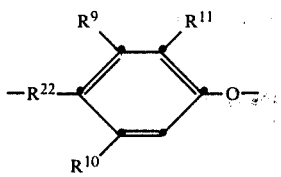
(29)

in which $R^{22}$ is $-O-$, $-S-$ or $=CR^{51}R^{61}$, in which $R^{51}$ and $R^{61}$ independently of one another are hydrogen or alkyl having 1 to 6 carbon atoms, and $R^9$, $R^{10}$ and $R^{11}$ are as defined in claim 10, or $L_4$ is of the formula

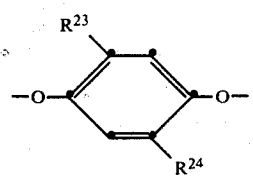
(30)

in which $R^{23}$ and $R^{24}$ independently of one another are hydrogen, substituted or unsubstituted alkyl having 1 to 18 carbon atoms or substituted or unsubstituted alkoxy having 1 to 4 carbon atoms, and $R'$, $R''$, x and y are as defined in claim 13.

15. A photographic recording material according to claim 14, wherein the development accelerator is of the formula

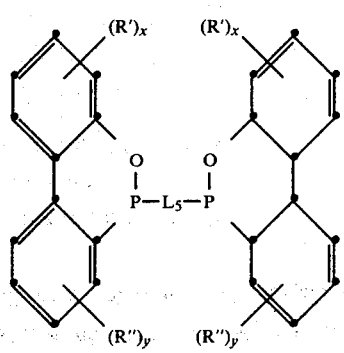
(31)

in which $L_5$ is a radical of the formula $=N-Z_3$, in which $Z_3$ is as defined in claim 14, or is a radical of the formulae

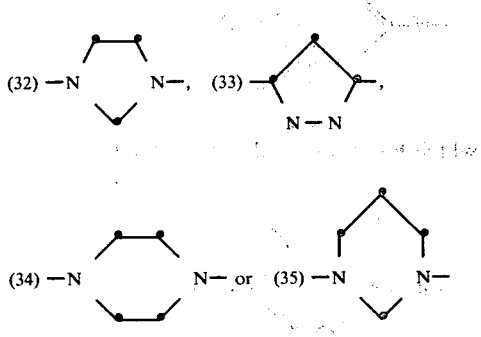

or $L_5$ is of the formula

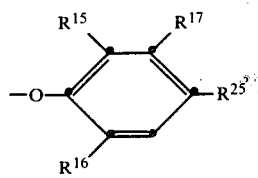

in which $R^{25}$ is a radical of the formulae

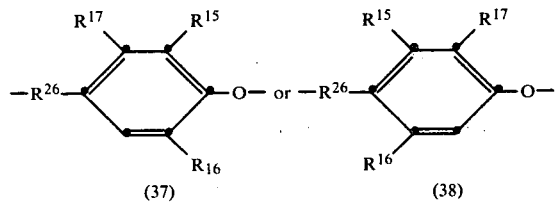

in which $R^{26}$ is $=CR^{51}R^{61}$, in which $R^{51}$ and $R^{61}$ are as defined in claim 14, and $R^{15}$, $R^{16}$ and $R^{17}$ are as defined in claim 11, or $L_5$ is a radical of the formula

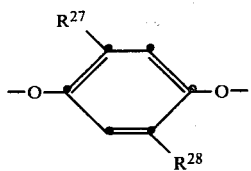

in which $R^{27}$ and $R^{28}$ independently of one another are hydrogen, alkyl having 1 to 12 carbon atoms or alkoxy having 1 to 4 carbon atoms, and R', R", x and y are as defined in claim 14.

16. A photographic recording material according to claim 15, wherein the development accelerator is of the formula

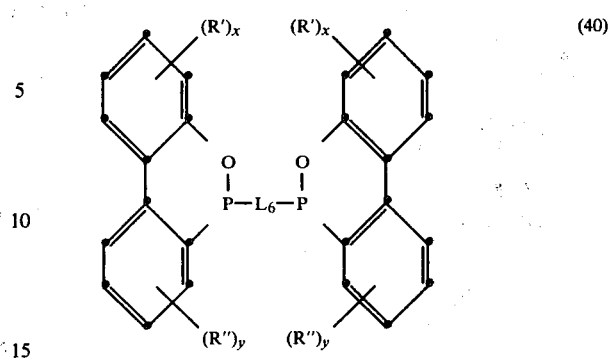

in which $L_6$ is a radical of the formula $=N-Z_3$, in which $Z_3$ is as defined in claim 15, or is a radical of the formulae

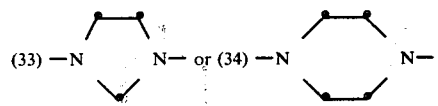

or $L_6$ is of the formula

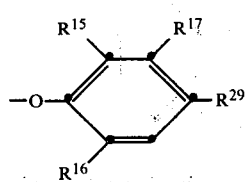

in which $R^{29}$ is a radical of the formulae

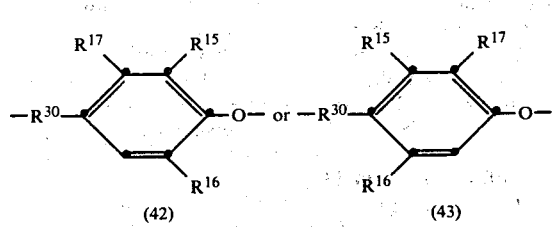

in which $R^{30}$ is $=CR^{51}R^{61}$ and $R^{15}$, $R^{16}$ and $R^{17}$ as well as $R^{51}$ and $R^{61}$ are as defined in claim 15, or $L_6$ is of the formula

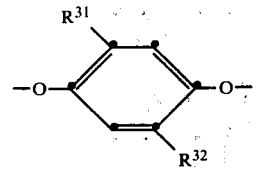

in which $R^{31}$ and $R^{32}$ independently of one another are hydrogen or alkyl having 1 to 12 carbon atoms, and R', R", x and y are as defined in claim 15.

17. A photographic recording material according to claim 16, wherein the development accelerator is of the formula

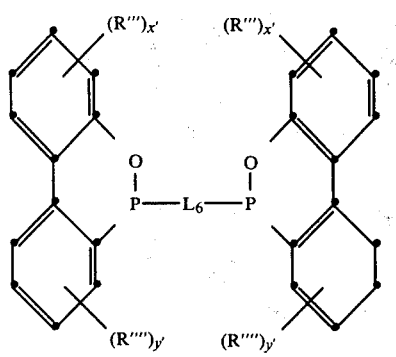
(45)

in which R''', R'''', x' and y' are as defined in claim 12 and L₆ is as defined in claim 16.

18. A photographic recording material according to claim 3, wherein the development accelerator is of the formula

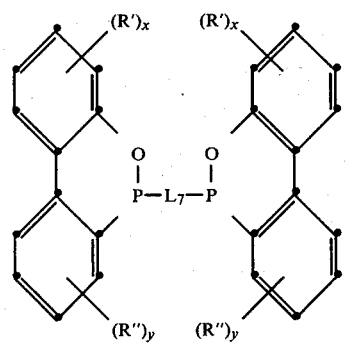
(46)

in which L₇ is a radical of the formula —NB₅—E₃—NB₆—, in which B₅ and B₆ independently of one another are hydrogen, methyl, ethyl or the radical A and in which E₃ is alkylene having 1 to 6 carbon atoms or

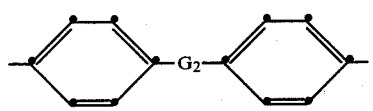

in which G₂ is —O—, —S, or =CK₃K₄, in which K₃ and K₄ independently of one another are hydrogen or alkyl having 1 to 4 carbon atoms, and R', R'', x and y are as defined in claim 16.

19. A photographic recording material according to claim 18, wherein the development accelerator is of the formula

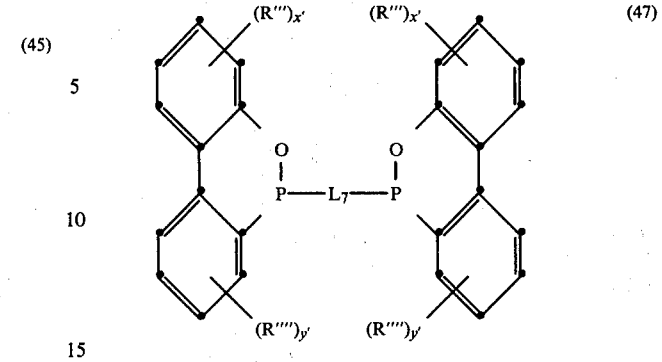
(47)

in which R''', R'''', x', y' are as defined in claim 17 and L₇ is as defined in claim 18.

20. A photographic recording material according to claim 1, wherein the development accelerator is of the formula

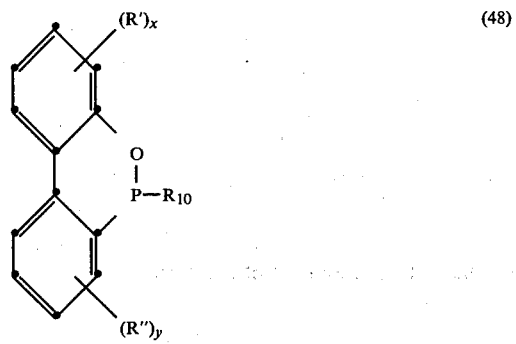
(48)

in which R₁₀ is of the formula

(49)

in which $R^{71}$ is hydrogen, alkyl having 1 to 12 carbon atoms, cyclohexyl or cyclooctyl and $R^{81}$ is alkyl having 1 to 12 carbon atoms, cyclohexyl, cyclooctyl, alkenyl having 2 to 6 carbon atoms, phenyl which is unsubstituted or substituted by alkyl having 1 to 6 carbon atoms and which can carry 1 or 2 such alkyl substituents, or is piperidinyl which is unsubstituted or substituted by alkyl having 1 to 4 carbon atoms and which can carry 1 to 4 such alkyl substituents, or in which $R^{81}$ and $R^{71}$ conjointly form a radical of the formulae —(CH₂)₄—, —(CH₂)₅—, —CH₂CH₂—O—CH₂CH₂— or —CH₂CH₂—NH—CH₂CH₂—, or in which R₁₀ is of the formula

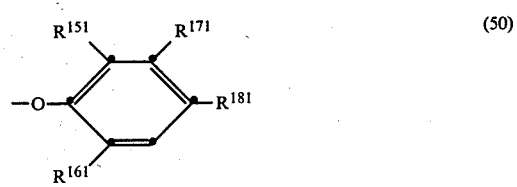
(50)

in which $R^{151}$ and $R^{161}$ independently of one another are hydrogen, alkyl having 1 to 8 carbon atoms, benzyl or phenylethyl, it being possible for the phenyl radicals to be substituted by alkyl having 1 to 4 carbon atoms, $R^{171}$ is hydrogen, methyl or ethyl and $R^{181}$ is hydrogen, alkyl having 1 to 8 carbon atoms, which is unsubstituted or substituted by carbalkoxy having 2 to 24 carbon atoms, or is alkoxy having 1 to 8 carbon atoms or carbalkoxy having 2 to 19 carbon atoms, or $R^{181}$ conjointly with $R^{171}$ represents those atoms which are required in order to form, together with the carbon atoms to which they are bonded, a saturated 5-membered ring which is unsubstituted or substituted by alkyl having 1 to 4 carbon atoms and which can be substituted by up to 4 such alkyl substituents, or in which $R_{10}$ is of the formula

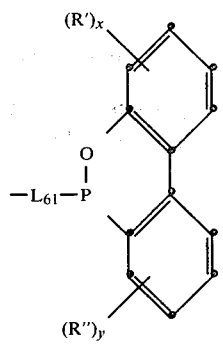 (51)

in which $L_{61}$ is a radical of the formula $=N-Z_4$, in which $Z_4$ is alkyl having 1 to 12 carbon atoms or cyclohexyl, or $L_{61}$ is a radical of the formulae

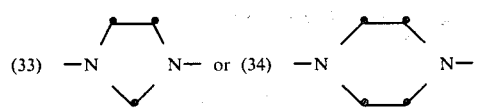

or

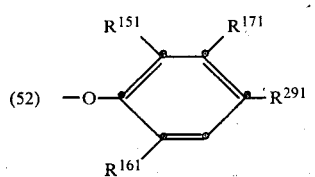 (52)

in which $R^{291}$ is a radical of the formulae

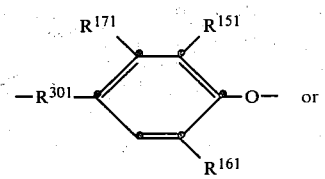 (53)

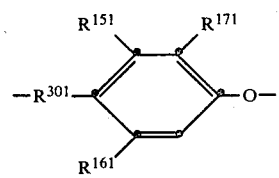 (54)

in which $R^{301}$ is $=CR^{52}R^{62}$, in which $R^{52}$ and $R^{62}$ independently of one another are hydrogen or alkyl having 1 to 4 carbon atoms, or in which $L_{61}$ is of the formula

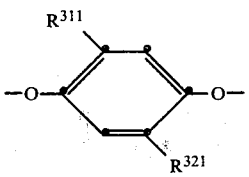 (55)

in which $R^{311}$ and $R^{321}$ independently of one another are hydrogen or alkyl having 1 to 8 carbon atoms, or in which $R_{10}$ is of the formula

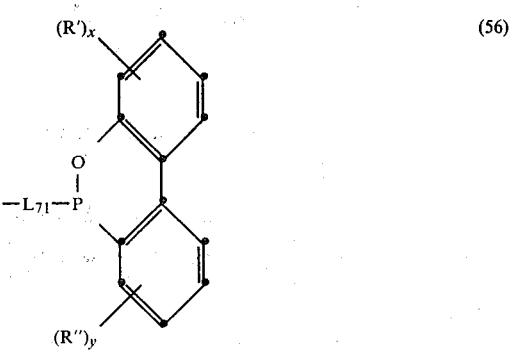 (56)

in which $L_{71}$ is a radical of the formula $-NB_7-E_4-NB_8$, in which $B_7$ and $B_8$ independently of one another are hydrogen or the radical A, and $E_4$ *L is alkylene having* 1 to 6 carbon atoms or

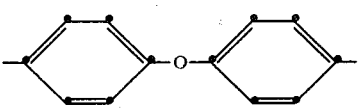

and in which R', R'', x and y are as defined in claim 18.

21. A photographic recording material according to claim 20, wherein the development accelerator is of the formula

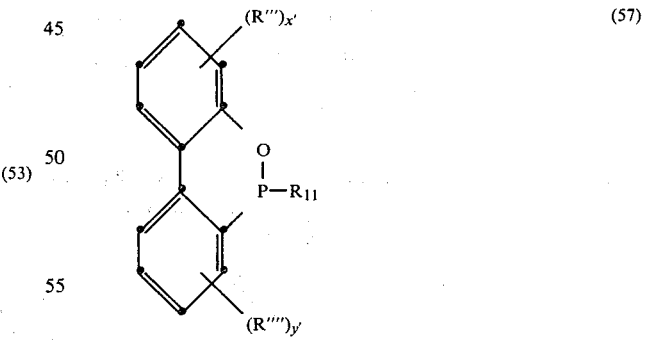 (57)

in which $R_{11}$ is of the formula

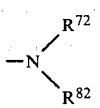 (58)

in which $R^{72}$ is hydrogen, alkyl having 1 to 8 carbon atoms or cyclohexyl and $R^{82}$ is alkyl having 1 to 8 carbon atoms, cyclohexyl, allyl, phenyl which is unsubstituted or substituted by alkyl having 1 to 4 carbon atoms and which can carry 1 or 2 such alkyl substituents, or is piperidin-4-yl which is unsubstituted or substituted by methyl and which can carry 1 to 4 methyl groups, or in which $R^{82}$ and $R^{72}$ conjointly form a radical of the formulae —(CH$_2$)$_5$— or —CH$_2$CH$_2$—NH—CH$_2$CH$_2$—, or in which R$_{11}$ is of the formula

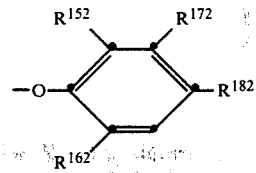
(59)

in which $R^{152}$ and $R^{162}$ independently of one another are hydrogen, alkyl having 1 to 8 carbon atoms or benzyl, wherein the phenyl radical can be substituted by methyl groups, $R^{172}$ is hydrogen or methyl and $R^{182}$ is hydrogen, alkyl having 1 to 8 atoms, alkyl having 1 to 4 carbon atoms, which is substituted by carbalkoxy having 2 to 19 carbon atoms, or is methoxy or carbalkoxy having 2 to 19 carbon atoms, or $R^{182}$ conjointly with $R^{172}$ represents those atoms which are required in order to form, together with the carbon atoms to which they are bonded, a saturated 5-membered ring which is unsubstituted or substituted by 1 to 4 methyl groups, or in which R$_{11}$ is of the formula

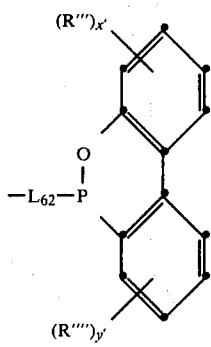
(60)

in which L$_{62}$ is a radical of the formula =N—Z$_4$, with Z$_4$ being as defined in claim 20, or is of the formula

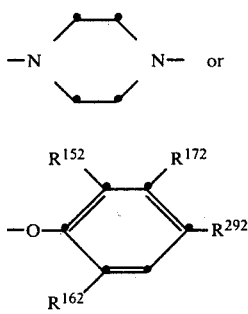
(34)

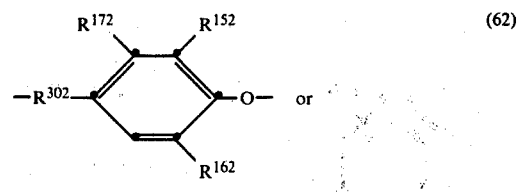
(61)

in which $R^{292}$ is a radical of the formulae

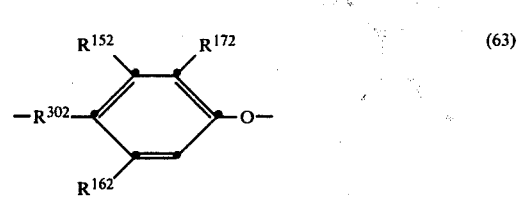
(62)

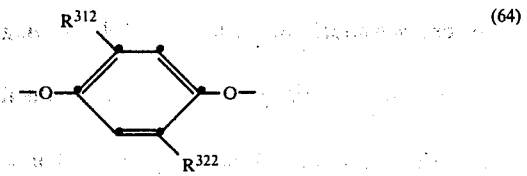
(63)

in which $R^{302}$ is —CH$_2$—, —CHCH$_3$— or C(CH$_3$)$_2$—, or in which L$_{62}$ is of the formula

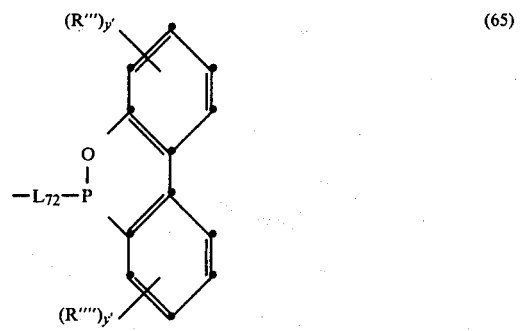
(64)

in which $R^{312}$ and $R^{322}$ independently of one another are hydrogen or alkyl having 1 to 4 carbon atoms, or in which R$_{11}$ is of the formula (65)

in which L$_{72}$ is a radical of the formula —NB$_7$—E$_5$—NB$_8$—, in which B$_7$ and B$_8$ are as defined in claim 20 and E$_5$ is alkylene having 1 to 6 carbon atoms, and in which R''', R'''', x' and y' are as defined in claim 19.

22. A developing bath for photographic silver halide recording material, which both contains a silver halide developing agent and a development accelerator in a quantity of 1 to 50 g per mol of silver halide in said photographic silver halide recording material, said development accelerator is of the formula

A—R (1)

in which A is a dibenzo[c,e][1,2]oxaphosphorine radical of the formula

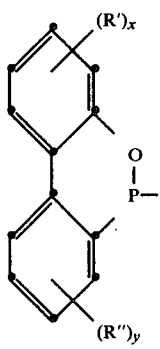

in which R' and R" independently of one another are hydrogen, substituted or unsubstituted alkyl having 1 to 4 carbon atoms or halogen, x and y independently of one another are 0, 1, 2 or 3 and R is substituted or unsubstituted amino, substituted or unsubstituted cyclic amino, substituted or unsubstituted aryloxy or a group of the formula

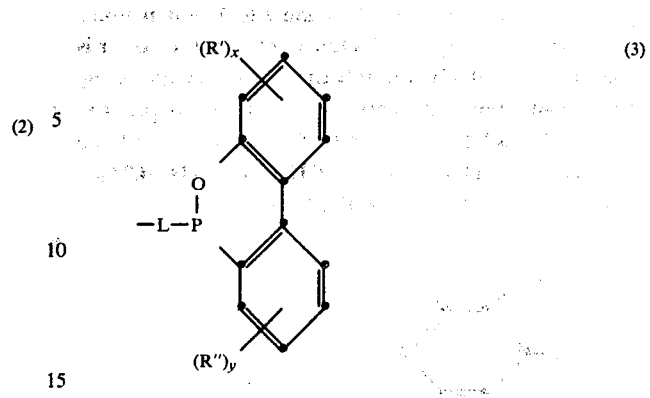

in which L is a radical of the formula =N—Z, with Z being substituted or unsubstituted alkyl or cycloalkyl, or a substituted or unsubstituted 5-membered or 6-membered, saturated or unsaturated ring which contains at least 2 hetero-atoms and which is bonded to the oxaphosphorine radicals via the hetero-atoms, or substituted or unsubstituted aryleneoxy, substituted or unsubstituted oxyaryleneoxy or a radical of the formula —NB$_1$—E—NB$_2$, in which B$_1$ and B$_2$ independently of one another are hydrogen, alkyl or the radical A and E is alkylene or

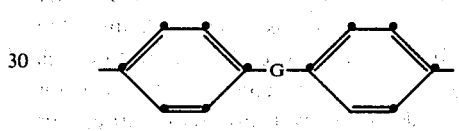

in which G is —O—, —S— or alkylene, and R', R", x and y are as defined above.

* * * * *

UNITED STATES PATENT AND TRADEMARK OFFICE
CERTIFICATE OF CORRECTION

PATENT NO. : 4,407,935

DATED : October 4, 1983

INVENTOR(S) : Mario Fryberg et al

It is certified that error appears in the above-identified patent and that said Letters Patent is hereby corrected as shown below:

| | |
|---|---|
| Col. 6, line 14 | Delete "$-R_{12}$" and insert -- $-R_{21}$ -- |
| Col. 17, line 26 | After "$L_6$" insert --is-- |
| Col. 17, line 38 | After "radical" delete "or" and insert --of-- |
| Col. 34, line 30 | Insert --(15)-- next to formula |
| Col. 36, line 66 | Delete "phorographic" and insert --photographic-- |
| Col. 44, line 31 | After "$E_4$" delete "L" |

Signed and Sealed this

Twenty-seventh Day of December 1983

[SEAL]

Attest:

GERALD J. MOSSINGHOFF

Attesting Officer

Commissioner of Patents and Trademarks